(12) United States Patent
Guy et al.

(10) Patent No.: US 12,427,160 B2
(45) Date of Patent: Sep. 30, 2025

(54) USE OF CANNABINOIDS IN THE TREATMENT OF EPILEPSY

(71) Applicant: Jazz Pharmaceuticals Research UK Limited, Sittingbourne (GB)

(72) Inventors: Geoffrey Guy, Cambridge (GB); Stephen Wright, Altrincham (GB); Orrin Devinsky, New York, NY (US)

(73) Assignee: JAZZ PHARMACEUTICALS RESEARCH UK LIMITED, Sittingbourne (GB)

( * ) Notice: Subject to any disclaimer, the term of this patent is extended or adjusted under 35 U.S.C. 154(b) by 0 days.

(21) Appl. No.: 19/187,858

(22) Filed: Apr. 23, 2025

(65) Prior Publication Data

US 2025/0248950 A1  Aug. 7, 2025

Related U.S. Application Data

(63) Continuation of application No. 18/186,792, filed on Mar. 20, 2023, which is a continuation of application No. 17/819,046, filed on Aug. 11, 2022, now Pat. No. 11,633,369, which is a continuation of application No. 17/477,172, filed on Sep. 16, 2021, now Pat. No. 11,446,258, which is a continuation of application No. 17/242,075, filed on Apr. 27, 2021, now Pat. No. 11,154,517, which is a continuation of application No. 17/198,965, filed on Mar. 11, 2021, now Pat. No. 11,096,905, which is a continuation of application No. 16/911,914, filed on Jun. 25, 2020, now Pat. No. 10,966,939, which is a continuation of application No. 16/198,141, filed on Nov. 21, 2018, now Pat. No. 10,849,860, which is a continuation of application No. 15/449,535, filed on Mar. 3, 2017, now Pat. No. 10,137,095, which is a continuation of application No. 14/881,969, filed on Oct. 13, 2015, now Pat. No. 10,111,840.

(30) Foreign Application Priority Data

Oct. 14, 2014  (GB) ...................... 1418171

(51) Int. Cl.
| | | |
|---|---|---|
| A61K 31/045 | (2006.01) | |
| A61K 9/08 | (2006.01) | |
| A61K 31/05 | (2006.01) | |
| A61K 31/352 | (2006.01) | |
| A61K 45/06 | (2006.01) | |
| A61K 47/10 | (2017.01) | |
| A61P 25/08 | (2006.01) | |

(52) U.S. Cl.
CPC ............. A61K 31/05 (2013.01); A61K 9/08 (2013.01); A61K 31/352 (2013.01); A61K 45/06 (2013.01); A61K 47/10 (2013.01)

(58) Field of Classification Search
CPC .............................. A61K 31/045; A61P 25/08
USPC ......................................................... 514/729
See application file for complete search history.

(56) References Cited

U.S. PATENT DOCUMENTS

| | | |
|---|---|---|
| 2,304,669 A | 12/1942 | Roger |
| 6,383,513 B1 | 5/2002 | Watts et al. |
| 6,403,126 B1 | 6/2002 | Webster et al. |
| 6,949,582 B1 | 9/2005 | Wallace |
| 7,025,992 B2 | 4/2006 | Whittle et al. |
| 8,222,292 B2 | 7/2012 | Goskonda et al. |
| 8,293,786 B2 | 10/2012 | Stinchcomb et al. |
| 8,603,515 B2 | 12/2013 | Whittle |
| 8,632,825 B2 | 1/2014 | Velasco Diez et al. |
| 8,673,368 B2 | 3/2014 | Guy et al. |
| 8,790,719 B2 | 7/2014 | Parolaro et al. |
| 9,017,737 B2 | 4/2015 | Kikuchi et al. |
| 9,023,322 B2 | 5/2015 | Van et al. |
| 9,066,920 B2 | 6/2015 | Whalley et al. |
| 9,095,554 B2 | 8/2015 | Lewis et al. |
| 9,095,555 B2 | 8/2015 | Winnicki |
| 9,125,859 B2 | 9/2015 | Whalley et al. |
| 9,168,278 B2 | 10/2015 | Guy et al. |
| 9,259,449 B2 | 2/2016 | Raderman |
| 9,474,726 B2 | 10/2016 | Guy et al. |
| 9,477,019 B2 | 10/2016 | Li et al. |
| 9,492,438 B2 | 11/2016 | Pollard |
| 9,522,123 B2 | 12/2016 | Whalley et al. |

(Continued)

FOREIGN PATENT DOCUMENTS

| | | |
|---|---|---|
| CA | 2737447 A1 | 10/2012 |
| CA | 2859934 A1 | 3/2016 |

(Continued)

OTHER PUBLICATIONS

Aagaard, L. et al., "Adverse Drug Reactions in the Paediatric Population in Denmark: A Retrospective Analysis of Reports Made to the Danish Medicines Agency from 1998 to 2007," Drug Saf, 33(4):327-339 (2010).

(Continued)

Primary Examiner — Raymond J Henley, III
(74) Attorney, Agent, or Firm — COOLEY LLP

(57) ABSTRACT

The present disclosure relates to the use of cannabidiol (CBD) for the treatment of atonic seizures. In particular the CBD appears particularly effective in reducing atonic seizures in patients suffering with etiologies that include: Lennox-Gastaut Syndrome; Tuberous Sclerosis Complex; Dravet Syndrome; Doose Syndrome; Aicardi syndrome; CDKL5 and Dup15q in comparison to other seizure types. The disclosure further relates to the use of CBD in combination with one or more anti-epileptic drugs (AEDs).

29 Claims, 1 Drawing Sheet

(56) References Cited

U.S. PATENT DOCUMENTS

| | | | |
|---|---|---|---|
| 9,630,941 B2 | 4/2017 | Elsohly et al. | |
| 9,675,654 B2 | 6/2017 | Parolaro et al. | |
| 9,680,796 B2 | 6/2017 | Miller et al. | |
| 9,730,911 B2 | 8/2017 | Verzura et al. | |
| 9,949,936 B2 | 4/2018 | Guy et al. | |
| 9,949,937 B2 | 4/2018 | Guy et al. | |
| 9,956,183 B2 | 5/2018 | Guy et al. | |
| 9,956,184 B2 | 5/2018 | Guy et al. | |
| 9,956,185 B2 | 5/2018 | Guy et al. | |
| 9,956,186 B2 | 5/2018 | Guy et al. | |
| 9,962,341 B2 | 5/2018 | Stott et al. | |
| 10,039,724 B2 | 8/2018 | Stott et al. | |
| 10,092,525 B2 | 10/2018 | Guy et al. | |
| 10,098,867 B2 | 10/2018 | Javid et al. | |
| 10,111,840 B2 * | 10/2018 | Guy | A61P 25/00 |
| 10,137,095 B2 * | 11/2018 | Guy | A61K 31/05 |
| 10,220,005 B2 | 3/2019 | Martinez-Orgado et al. | |
| 10,226,433 B2 | 3/2019 | Di Marzo et al. | |
| 10,583,096 B2 | 3/2020 | Guy et al. | |
| 10,603,288 B2 | 3/2020 | Guy et al. | |
| 10,653,641 B2 | 5/2020 | Robson et al. | |
| 10,709,671 B2 | 7/2020 | Guy et al. | |
| 10,709,673 B2 | 7/2020 | Guy | |
| 10,709,674 B2 | 7/2020 | Guy et al. | |
| 10,729,665 B2 | 8/2020 | Whalley et al. | |
| 10,758,514 B2 | 9/2020 | Liu et al. | |
| 10,765,643 B2 | 9/2020 | Guy et al. | |
| 10,799,467 B2 | 10/2020 | Whalley et al. | |
| 10,807,777 B2 | 10/2020 | Whittle | |
| 10,849,860 B2 * | 12/2020 | Guy | A61K 31/352 |
| 10,918,608 B2 | 2/2021 | Guy et al. | |
| 10,925,525 B2 | 2/2021 | Nakaji | |
| 10,966,939 B2 * | 4/2021 | Guy | A61P 25/08 |
| 11,000,486 B2 | 5/2021 | Wright et al. | |
| 11,065,209 B2 | 7/2021 | Guy et al. | |
| 11,065,227 B2 | 7/2021 | Stott et al. | |
| 11,096,905 B2 * | 8/2021 | Guy | A61K 47/10 |
| 11,147,776 B2 | 10/2021 | Stott et al. | |
| 11,147,783 B2 | 10/2021 | Stott et al. | |
| 11,154,516 B2 | 10/2021 | Guy et al. | |
| 11,154,517 B2 * | 10/2021 | Guy | A61K 47/10 |
| 11,160,757 B1 | 11/2021 | Wilkhu et al. | |
| 11,160,795 B2 | 11/2021 | Guy et al. | |
| 11,207,292 B2 | 12/2021 | Guy et al. | |
| 11,224,600 B2 | 1/2022 | Blomgren et al. | |
| 11,229,612 B2 | 1/2022 | Wright et al. | |
| 11,291,631 B2 | 4/2022 | Shah | |
| 11,311,498 B2 | 4/2022 | Guy et al. | |
| 11,318,109 B2 | 5/2022 | Whalley et al. | |
| 11,331,279 B2 | 5/2022 | Vangara et al. | |
| 11,357,741 B2 | 6/2022 | Guy et al. | |
| 11,400,055 B2 | 8/2022 | Guy et al. | |
| 11,406,623 B2 | 8/2022 | Guy et al. | |
| 11,413,266 B2 | 8/2022 | Biró et al. | |
| 11,419,829 B2 | 8/2022 | Whalley et al. | |
| 11,426,362 B2 | 8/2022 | Wright et al. | |
| 11,446,258 B2 * | 9/2022 | Guy | A61P 25/00 |
| 11,590,087 B2 | 2/2023 | Guy et al. | |
| 11,633,369 B2 * | 4/2023 | Guy | A61K 31/352 514/94 |
| 11,679,087 B2 | 6/2023 | Guy et al. | |
| 11,684,598 B2 | 6/2023 | Stott et al. | |
| 11,701,330 B2 | 7/2023 | Guy et al. | |
| 11,709,671 B2 | 7/2023 | Joubert et al. | |
| 11,766,411 B2 | 9/2023 | Guy et al. | |
| 11,793,770 B2 | 10/2023 | Stott et al. | |
| 11,806,319 B2 | 11/2023 | Wilkhu et al. | |
| 11,865,102 B2 | 1/2024 | Guy et al. | |
| 11,963,937 B2 | 4/2024 | Guy | |
| 12,023,305 B2 | 7/2024 | Whalley et al. | |
| 12,064,398 B2 | 8/2024 | Wright et al. | |
| 12,064,399 B2 | 8/2024 | Guy et al. | |
| 12,102,619 B2 | 10/2024 | Guy et al. | |
| 12,121,499 B2 | 10/2024 | Whalley et al. | |
| 12,161,607 B2 | 12/2024 | Wright et al. | |
| 12,213,985 B2 | 2/2025 | Shah | |
| 12,263,139 B2 | 4/2025 | Whalley et al. | |
| 12,318,356 B2 | 6/2025 | Guy | |
| 2004/0034108 A1 | 2/2004 | Whittle | |
| 2004/0049059 A1 | 3/2004 | Mueller | |
| 2004/0110828 A1 | 6/2004 | Chowdhury et al. | |
| 2004/0147767 A1 | 7/2004 | Whittle et al. | |
| 2005/0042172 A1 | 2/2005 | Whittle | |
| 2005/0266108 A1 | 12/2005 | Flockhart et al. | |
| 2006/0039959 A1 | 2/2006 | Wessling | |
| 2006/0167283 A1 | 7/2006 | Flockhart et al. | |
| 2007/0060638 A1 | 3/2007 | Olmstead et al. | |
| 2007/0099987 A1 | 5/2007 | Weiss et al. | |
| 2007/0238786 A1 | 10/2007 | Hobden et al. | |
| 2008/0112895 A1 | 5/2008 | Kottayil et al. | |
| 2008/0119544 A1 | 5/2008 | Guy et al. | |
| 2008/0188461 A1 | 8/2008 | Guan et al. | |
| 2009/0036523 A1 | 2/2009 | Stinchcomb et al. | |
| 2009/0264063 A1 | 10/2009 | Tinsley et al. | |
| 2009/0306221 A1 | 12/2009 | Guy et al. | |
| 2010/0239693 A1 | 9/2010 | Guy et al. | |
| 2010/0273895 A1 | 10/2010 | Stinchcomb et al. | |
| 2010/0317729 A1 | 12/2010 | Guy et al. | |
| 2011/0028431 A1 | 2/2011 | Zerbe et al. | |
| 2011/0033529 A1 | 2/2011 | Samantaray et al. | |
| 2011/0038958 A1 | 2/2011 | Kikuchi et al. | |
| 2011/0065747 A1 | 3/2011 | Donello et al. | |
| 2011/0082195 A1 | 4/2011 | Guy et al. | |
| 2011/0150825 A1 | 6/2011 | Buggy et al. | |
| 2011/0172262 A1 | 7/2011 | Deftereos et al. | |
| 2012/0004251 A1 | 1/2012 | Whalley et al. | |
| 2012/0165402 A1 | 6/2012 | Whalley et al. | |
| 2012/0183606 A1 | 7/2012 | Bender et al. | |
| 2012/0202891 A1 | 8/2012 | Stinchcomb et al. | |
| 2012/0270845 A1 | 10/2012 | Bannister et al. | |
| 2013/0143894 A1 | 6/2013 | Bergstrom et al. | |
| 2013/0209483 A1 | 8/2013 | McAllister | |
| 2013/0245110 A1 | 9/2013 | Guy et al. | |
| 2013/0296398 A1 | 11/2013 | Whalley et al. | |
| 2014/0100269 A1 | 4/2014 | Goskonda et al. | |
| 2014/0155456 A9 | 6/2014 | Whalley et al. | |
| 2014/0243405 A1 | 8/2014 | Whalley et al. | |
| 2014/0335208 A1 | 11/2014 | Cawthorne et al. | |
| 2014/0343044 A1 | 11/2014 | Ceulemens et al. | |
| 2015/0111939 A1 | 4/2015 | Gruening et al. | |
| 2015/0181924 A1 | 7/2015 | Llamas | |
| 2015/0320698 A1 | 11/2015 | Whalley et al. | |
| 2015/0335590 A1 | 11/2015 | Whalley et al. | |
| 2015/0342902 A1 | 12/2015 | Vangara et al. | |
| 2015/0343071 A1 | 12/2015 | Vangara et al. | |
| 2015/0359755 A1 | 12/2015 | Guy et al. | |
| 2015/0359756 A1 | 12/2015 | Guy et al. | |
| 2016/0010126 A1 | 1/2016 | Poulos et al. | |
| 2016/0166498 A1 | 6/2016 | Anastassov et al. | |
| 2016/0166514 A1 | 6/2016 | Guy et al. | |
| 2016/0166515 A1 | 6/2016 | Guy et al. | |
| 2016/0220529 A1 | 8/2016 | Guy et al. | |
| 2016/0256411 A1 | 9/2016 | Aung-Din | |
| 2016/0317468 A1 | 11/2016 | Sankar et al. | |
| 2016/0338974 A1 | 11/2016 | Aung-Din | |
| 2017/0007551 A1 | 1/2017 | Guy et al. | |
| 2017/0008868 A1 | 1/2017 | Dialer et al. | |
| 2017/0172939 A1 | 6/2017 | Guy et al. | |
| 2017/0172940 A1 | 6/2017 | Guy et al. | |
| 2017/0172941 A1 | 6/2017 | Guy et al. | |
| 2017/0173043 A1 | 6/2017 | Guy et al. | |
| 2017/0173044 A1 | 6/2017 | Guy et al. | |
| 2017/0181982 A1 | 6/2017 | Guy et al. | |
| 2017/0224634 A1 | 8/2017 | Vangara et al. | |
| 2017/0231923 A1 | 8/2017 | Guy et al. | |
| 2017/0239193 A1 | 8/2017 | Guy et al. | |
| 2017/0246121 A1 | 8/2017 | Guy et al. | |
| 2017/0266126 A1 | 9/2017 | Guy et al. | |
| 2017/0273913 A1 | 9/2017 | Whalley et al. | |
| 2018/0028489 A1 | 2/2018 | Vangara et al. | |
| 2018/0071210 A1 | 3/2018 | Wilkhu et al. | |
| 2018/0228751 A1 | 8/2018 | Stott et al. | |
| 2018/0338931 A1 | 11/2018 | Guy et al. | |
| 2019/0031601 A1 | 1/2019 | Elsohly et al. | |

(56) References Cited

U.S. PATENT DOCUMENTS

| | | |
|---|---|---|
| 2019/0083418 A1 | 3/2019 | Guy et al. |
| 2019/0091171 A1 | 3/2019 | Guy et al. |
| 2019/0160393 A1 | 5/2019 | Marshall et al. |
| 2019/0167583 A1 | 6/2019 | Shah |
| 2019/0175547 A1 | 6/2019 | Stott et al. |
| 2019/0247324 A1 | 8/2019 | Whalley et al. |
| 2019/0314296 A1 | 10/2019 | Wright et al. |
| 2019/0321307 A1 | 10/2019 | Guy et al. |
| 2019/0365667 A1 | 12/2019 | Wright et al. |
| 2020/0000741 A1 | 1/2020 | Guy et al. |
| 2020/0069608 A1 | 3/2020 | Guy et al. |
| 2020/0138738 A1 | 5/2020 | Guy et al. |
| 2020/0179303 A1 | 6/2020 | Guy et al. |
| 2020/0206152 A1 | 7/2020 | Stott et al. |
| 2020/0206153 A1 | 7/2020 | Whalley et al. |
| 2020/0237683 A1 | 7/2020 | Whalley et al. |
| 2020/0297656 A1 | 9/2020 | Guy et al. |
| 2020/0323792 A1 | 10/2020 | Guy et al. |
| 2020/0352878 A1 | 11/2020 | Guy et al. |
| 2020/0368179 A1 | 11/2020 | Guy et al. |
| 2021/0015789 A1 | 1/2021 | Guy et al. |
| 2021/0052512 A1 | 2/2021 | Guy et al. |
| 2021/0059949 A1 | 3/2021 | Wilkhu et al. |
| 2021/0059960 A1 | 3/2021 | Wilkhu et al. |
| 2021/0059976 A1 | 3/2021 | Wilkhu et al. |
| 2021/0069333 A1 | 3/2021 | Velasco Diez et al. |
| 2021/0093581 A1 | 4/2021 | Guy et al. |
| 2021/0100755 A1 | 4/2021 | Whalley et al. |
| 2021/0145765 A1 | 5/2021 | Guy et al. |
| 2021/0167950 A1 | 6/2021 | Arkko et al. |
| 2021/0169824 A1 | 6/2021 | Guy et al. |
| 2021/0177773 A1 | 6/2021 | Guy et al. |
| 2021/0196651 A1 | 7/2021 | Guy et al. |
| 2021/0230145 A1 | 7/2021 | Blankman et al. |
| 2021/0244685 A1 | 8/2021 | Guy et al. |
| 2021/0290565 A1 | 9/2021 | Guy et al. |
| 2021/0308072 A1 | 10/2021 | Wright et al. |
| 2021/0330636 A1 | 10/2021 | Guy et al. |
| 2021/0401771 A1 | 12/2021 | Guy et al. |
| 2022/0000800 A1 | 1/2022 | Guy et al. |
| 2022/0008355 A1 | 1/2022 | Guy et al. |
| 2022/0016048 A1 | 1/2022 | Guy et al. |
| 2022/0023232 A1 | 1/2022 | Guy et al. |
| 2022/0040155 A1 | 2/2022 | Guy et al. |
| 2022/0062197 A1 | 3/2022 | Stott et al. |
| 2022/0062211 A1 | 3/2022 | Stott et al. |
| 2022/0087951 A1 | 3/2022 | Knappertz |
| 2022/0096397 A1 | 3/2022 | Wright et al. |
| 2022/0168266 A1 | 6/2022 | Guy et al. |
| 2022/0183997 A1 | 6/2022 | Guy et al. |
| 2022/0184000 A1 | 6/2022 | Guy et al. |
| 2022/0202738 A1 | 6/2022 | Guy et al. |
| 2022/0211629 A1 | 7/2022 | Wilkhu et al. |
| 2022/0226257 A1 | 7/2022 | Guy et al. |
| 2022/0233495 A1 | 7/2022 | Silcock et al. |
| 2022/0249396 A1 | 8/2022 | Guy et al. |
| 2022/0257529 A1 | 8/2022 | Guy et al. |
| 2022/0265573 A1 | 8/2022 | Guy et al. |
| 2022/0288055 A1 | 9/2022 | Silcock et al. |
| 2022/0323375 A1 | 10/2022 | Guy et al. |
| 2022/0362149 A1 | 11/2022 | Shah |
| 2022/0378714 A1 | 12/2022 | Guy et al. |
| 2022/0378715 A1 | 12/2022 | Guy et al. |
| 2022/0378717 A1 | 12/2022 | Guy et al. |
| 2022/0378738 A1 | 12/2022 | Guy et al. |
| 2022/0387347 A1 | 12/2022 | Whalley et al. |
| 2022/0387348 A1 | 12/2022 | Guy et al. |
| 2022/0395470 A1 | 12/2022 | Whalley et al. |
| 2022/0395471 A1 | 12/2022 | Guy et al. |
| 2023/0000789 A1 | 1/2023 | Guy et al. |
| 2023/0022487 A1 | 1/2023 | Guy et al. |
| 2023/0024312 A1 | 1/2023 | Whalley et al. |
| 2023/0026079 A1 | 1/2023 | Guy et al. |
| 2023/0032502 A1 | 2/2023 | Guy et al. |
| 2023/0038423 A1 | 2/2023 | Silcock et al. |
| 2023/0068885 A1 | 3/2023 | Guy et al. |
| 2023/0143812 A1 | 5/2023 | Knappertz et al. |
| 2023/0206209 A1 | 6/2023 | Janiga |
| 2023/0225986 A1 | 7/2023 | Li et al. |
| 2023/0235825 A1 | 7/2023 | Thompson et al. |
| 2023/0248664 A1 | 8/2023 | Guy et al. |
| 2023/0263744 A1 | 8/2023 | Guy |
| 2023/0277560 A1 | 9/2023 | Checketts et al. |
| 2023/0277561 A1 | 9/2023 | Checketts et al. |
| 2023/0277562 A1 | 9/2023 | Checketts et al. |
| 2023/0277563 A1 | 9/2023 | Checketts et al. |
| 2023/0285419 A1 | 9/2023 | Checketts et al. |
| 2023/0285420 A1 | 9/2023 | Checketts et al. |
| 2023/0285421 A1 | 9/2023 | Checketts et al. |
| 2023/0285422 A1 | 9/2023 | Checketts et al. |
| 2023/0285423 A1 | 9/2023 | Checketts et al. |
| 2023/0285424 A1 | 9/2023 | Checketts et al. |
| 2023/0285425 A1 | 9/2023 | Checketts et al. |
| 2023/0285426 A1 | 9/2023 | Checketts et al. |
| 2023/0285427 A1 | 9/2023 | Checketts et al. |
| 2023/0285428 A1 | 9/2023 | Checketts et al. |
| 2023/0301934 A1 | 9/2023 | Whalley et al. |
| 2023/0301936 A1 | 9/2023 | Guy et al. |
| 2023/0310464 A1 | 10/2023 | Checketts et al. |
| 2023/0346809 A1 | 11/2023 | Craig |
| 2023/0372367 A1 | 11/2023 | Checketts et al. |
| 2023/0372368 A1 | 11/2023 | Checketts et al. |
| 2024/0016819 A1 | 1/2024 | Craig |
| 2024/0025858 A1 | 1/2024 | Silcock et al. |
| 2024/0033229 A1 | 2/2024 | Guy et al. |
| 2024/0043388 A1 | 2/2024 | Silcock et al. |
| 2024/0050452 A1 | 2/2024 | Craig et al. |
| 2024/0091241 A1 | 3/2024 | Guy et al. |
| 2024/0130981 A1 | 4/2024 | Wilkhu |
| 2024/0131041 A1 | 4/2024 | Tse |
| 2024/0165048 A1 | 5/2024 | Guy |
| 2024/0207220 A1 | 6/2024 | Guy et al. |
| 2024/0215910 A1 | 7/2024 | Tse et al. |
| 2024/0226032 A9 | 7/2024 | Wilkhu et al. |
| 2024/0226123 A9 | 7/2024 | Tse |
| 2024/0238218 A1 | 7/2024 | Silcock et al. |
| 2024/0254066 A1 | 8/2024 | Silcock et al. |
| 2024/0254072 A1 | 8/2024 | Silcock et al. |
| 2024/0261234 A1 | 8/2024 | Guy |
| 2024/0293762 A1 | 9/2024 | Loft et al. |
| 2024/0350428 A1 | 10/2024 | Guy et al. |
| 2024/0360060 A1 | 10/2024 | Silcock et al. |
| 2025/0025482 A1 | 1/2025 | Knappertz |

FOREIGN PATENT DOCUMENTS

| | | |
|---|---|---|
| CN | 101040855 A | 9/2007 |
| CN | 103110582 A | 5/2013 |
| CN | 104490873 A | 4/2015 |
| CN | 108236608 A | 7/2018 |
| CN | 110215443 A | 9/2019 |
| CN | 110279617 A | 9/2019 |
| DE | 102012105063 A1 | 12/2013 |
| EP | 1542657 A1 | 6/2005 |
| EP | 2311475 A2 | 4/2011 |
| EP | 2578561 A1 | 4/2013 |
| EP | 2448637 B1 | 3/2014 |
| EP | 3157512 B1 | 4/2018 |
| GB | 2002754 A | 2/1979 |
| GB | 2377633 A | 1/2003 |
| GB | 2380129 A | 4/2003 |
| GB | 2381194 A | 4/2003 |
| GB | 2384707 A | 8/2003 |
| GB | 2434097 A | 7/2007 |
| GB | 2434312 A | 7/2007 |
| GB | 2438682 A | 12/2007 |
| GB | 2450753 A | 1/2009 |
| GB | 2456183 A | 7/2009 |
| GB | 2471523 A | 1/2011 |
| GB | 2478595 A | 9/2011 |
| GB | 2479153 A | 10/2011 |
| GB | 2485291 A | 5/2012 |
| GB | 2471565 B | 7/2012 |
| GB | 2487183 A | 7/2012 |

(56) References Cited

FOREIGN PATENT DOCUMENTS

| | | |
|---|---|---|
| GB | 2487712 A | 8/2012 |
| GB | 2478072 B | 12/2012 |
| GB | 2478074 B | 12/2012 |
| GB | 2492487 A | 1/2013 |
| GB | 2530001 A | 3/2016 |
| GB | 2531093 A | 4/2016 |
| GB | 2531278 A | 4/2016 |
| GB | 2531281 A | 4/2016 |
| GB | 2531282 A | 4/2016 |
| GB | 2539472 A | 12/2016 |
| GB | 2542155 A | 3/2017 |
| GB | 2551987 A | 1/2018 |
| GB | 2584140 A | 11/2020 |
| WO | WO-0195899 A2 | 12/2001 |
| WO | WO-02064109 A2 | 8/2002 |
| WO | WO-02089945 A2 | 11/2002 |
| WO | WO-03099302 A1 | 12/2003 |
| WO | WO-2004016246 A1 | 2/2004 |
| WO | WO-2004016277 A2 | 2/2004 |
| WO | WO-2004026802 A1 | 4/2004 |
| WO | WO-2005120478 A1 | 12/2005 |
| WO | WO-2006054057 A2 | 5/2006 |
| WO | WO-2006133941 A2 | 12/2006 |
| WO | WO-2007032962 A2 | 3/2007 |
| WO | WO-2007052013 A1 | 5/2007 |
| WO | WO-2007083098 A1 | 7/2007 |
| WO | WO-2007138322 A1 | 12/2007 |
| WO | WO-2008021394 A2 | 2/2008 |
| WO | WO-2008129258 A1 | 10/2008 |
| WO | WO-2008094181 A3 | 12/2008 |
| WO | WO-2008146006 A1 | 12/2008 |
| WO | WO-2009007697 A1 | 1/2009 |
| WO | WO-2009093018 A1 | 7/2009 |
| WO | WO-2011001169 A1 | 1/2011 |
| WO | WO-2011121351 A1 | 10/2011 |
| WO | WO-2012093255 A1 | 7/2012 |
| WO | WO-2012160358 A1 | 11/2012 |
| WO | WO-2013032351 A1 | 3/2013 |
| WO | WO-2013045891 A1 | 4/2013 |
| WO | WO-2014108899 A1 | 7/2014 |
| WO | WO-2014168131 A1 | 10/2014 |
| WO | WO-2015142501 A1 | 9/2015 |
| WO | WO-2015184127 A2 | 12/2015 |
| WO | WO-2015187988 A1 | 12/2015 |
| WO | WO-2015193667 A1 | 12/2015 |
| WO | WO-2015193668 A1 | 12/2015 |
| WO | WO-2016022936 A1 | 2/2016 |
| WO | WO-2016059399 A1 | 4/2016 |
| WO | WO-2016059403 A1 | 4/2016 |
| WO | WO-2016059405 A1 | 4/2016 |
| WO | WO-2016118391 A1 | 7/2016 |
| WO | WO-2016176279 A1 | 11/2016 |
| WO | WO-2016191651 A1 | 12/2016 |
| WO | WO-2016203239 A1 | 12/2016 |
| WO | WO-2017042567 A1 | 3/2017 |
| WO | WO-2017139496 A1 | 8/2017 |
| WO | WO-2017168138 A1 | 10/2017 |
| WO | WO-2017203529 A1 | 11/2017 |
| WO | WO-2017204986 A1 | 11/2017 |
| WO | WO-2018002665 A1 | 1/2018 |
| WO | WO-2018011808 A1 | 1/2018 |
| WO | WO-2018115962 A1 | 6/2018 |
| WO | WO-2018200024 A1 | 11/2018 |
| WO | WO-2018234811 A1 | 12/2018 |
| WO | WO-2019020738 A1 | 1/2019 |
| WO | WO-2019097238 A1 | 5/2019 |
| WO | WO-2019145700 A1 | 8/2019 |
| WO | WO-2019207319 A1 | 10/2019 |
| WO | WO-2019210210 A1 | 10/2019 |
| WO | WO-2019211795 A1 | 11/2019 |
| WO | WO-2020225540 A1 | 11/2020 |
| WO | WO-2020234569 A1 | 11/2020 |
| WO | WO-2021019231 A1 | 2/2021 |

OTHER PUBLICATIONS

AAN 67th Annual Meeting Abstract, Apr. 2015; https://www.aan.com/PressRoom/Home/GetDigitalAsset/11570, 1 page.

Abati, E. et al., "Cannabidiol treatment of refractory epileptic spasms: an open label study," American Epilepsy Society, Annual Meeting, Abstract 3.404, 2015, 2 pages; https://aesnet.org/abstractslisting/cannabidiol-treatment-of-refractory-epileptic-spasms--an-open-label-study.

Actiq (Oral Transmucosal Fentanyl Citrate), Clinical Pharmacology and Biopharmaceutics Review, Reviewer Suresh Doddapaneni, Ph.D., Center for Drug Evaluation and Research, Application No. NDA 20747, Submission Date: Nov. 11, 1996, Review Date: Apr. 22, 1997, 25 pages.

Adams, R. et al., "Isolation of Cannabinol, Cannabidiol and Quebrachitol from Red Oil of Minnesota Wild Hemp," J. Am. Chern. Soc. 1940, 62, 8, 2194-2196.

Advagraf 0.5 mg prolonged-release hard capsules, Advagraf 1 mg prolonged-release hard capsules, Advagraf 3 mg prolonged-release hard capsules, Advagraf 5 mg prolonged-release hard capsules, Annex 1—Summary of Product Characteristics, retrieved on Aug. 13, 2024, 60 pages.

Afinitor® (everolimus) tablets, for oral use, and Afinitor Disperz® (everolimus tablets for oral suspension) Prescribing Information, 2009, 49 pages.

Aker, R. G. et al., "Chemically Induced Experimental Models of Absence Epilepsy," Chemical-Induced Seizures: Mechanisms, Consequences and Treatment, Chapter 6, 2011, pp. 67-79.

Akiyama, M. et al., "Dravet Syndrome: A Genetic Epileptic Disorder," Acta Medicinae Okayama, 2012, vol. 66(5), pp. 369-376.

Alger, "Not too excited? Thank your endocannabinoids," Neuron, 51(4):393-595 (2006).

Allen G., "Florida Bill Would Allow Medical Marijuana For Child Seizures," Jan. 16, 2014, retrieved from https://www.npr.org/sections/health-shots/2014/01/16/262481852/florida-bill-would-allow-marijuana-extract-for-child-seizures, 16 pages.

Allen, J. W., "Clobazam as an adjunctive treatment in refractory epilepsy," British Medical Journal, 286:1246-1247 (1983).

Amada, N. et al., "Cannabidivarin (CBDV) suppresses pentylenetetrazole (PTZ)-induced increases in epilepsy-related gene expression," 2013, PeerJ, 1:e214; 18 pages; http://dx.doi.org/10.7717/peerj.214.

Anderson, C. L, "An Evaluation of Effectivness of Cannabidiol as an Antiepileptic Drug for Children with Intractable Generalized Epilepsy," Dissertation, University of Florida, 2017,130 pages;https://ufdc.ufl.edu/UFE0050852/00001 /pdf.

Andre, E. S. et al., "Spontaneous absence-like activity in Wistar rats: Behavioral and electrographic characteristics and the effects of antiepileptic drugs," Acta Scientiarum. Biological Sciences, 36(2):231-239 (2014).

[Anonymous], "Salutaris Drops Cannabidiol for Aicardi Syndrome—Salutaris Drops," Oct. 12, 2014; http://web.archive.org/web/20141012220050/ http://salutarisdrops.com/cannabidiol-aicardi-syndrome/, 3 pages.

[Anonymous], "GW Pharma Initiates Second Phase 3 Pivotal Study of Epidiolex® (CBD) in Lennox-Gastaut Syndrome," Jun. 11, 2015; https://www.benzinga.com/pressreleases/18/11/g12748407/gw-pharmaceuticals-announces-second-positive-phase-3-pivotal-trial-for, 5 pages.

[Anonymous], "GW Pharmaceuticals Announces Epidiolex Receives Fast Track Designation from FDA for the Treatment of Dravet Syndrome," GW Pharmaceuticals Press Release dated Jun. 6, 2014; http://www.gwpharm.com/GW%20Pharmaceuticals%20Announces%20Epidiolex%20Receives%20Fast%20Track%20Designation%20from%20FDA%20for%20the%20Treatment%20of%20Dravet%20Syndrome.aspx, 5 pages.

[Anonymous] "When to Expect Results from CW Hemp Oil", downloaded Sep. 5, 2017, https://www.cwhemp.com/blog/expecting-results-from-hemp, 9 pages.

Approval Letter for NDA 210365 Epidiolex, Jun. 25, 2018,12 pages.

Arik, A. E. et al., "Effect of levetiracetam on penicillin induced epileptic activity in rats," Acta Neurobiol Exp, 74:266-275 (2014).

(56) References Cited

OTHER PUBLICATIONS

Arzimanoglou et al., "All children who experience epileptic falls do not necessarily have Lennox-Gastaut syndrome . . . but many do," Epileptic Discord, 13:S3-S13 (2011).
Astruc-Diaz, F., "Cannabinoids delivery systems based on supramolecular inclusion complexes and polymeric nanocapsules for treatment of neuropathic pain," Université Claude Bernard—Lyon I, 2012, submitted on Jan. 23, 2014; https://tel.archives-ouvertes.fr/tel-00935588 [accessed Nov. 1, 2019], 278 pages.
[Author Unknown] "Clinical Drug Interaction Studies—Cytochrome P450 Enzyme—and Transporter-Mediated Drug Interactions Guidance for Industry", U.S. Department of Health and Human Services, Food and Drug Administration, Center for Drug Evaluation and Research (CDER), Clinical Pharmacology (Jan. 2020); 27 pages.
Babayeva et al., "Marijuana Compounds: A Non-Conventional Therapeutic Approach to Epilepsy in Children," J. Addict. Neuropharmacol, 1:1 (2014); doi:10.24966/AAD-7276/100002, 9 pages.
Bacca, A., "HempVap from HempMedsPX," Mar. 10, 2014; https://cannabisnow.com/hempvap-from-hempmedspx/, 3 pages.
Bancaud, J. et al., "Proposal for revised clinical and electroencephalographic classification of epileptic seizures. From the Commission on Classification and Terminology of the International League Against Epilepsy," Epilepsia, Aug. 1981;22(4):489-501. doi: 10.1111/j.1528-1157.1981.tb06159.x.
Banerjee et al., "Case Report: Aicardi syndrome: A report of five Indian cases," Neurology India, 54(1):91-93 (2006).
Barton, M. E. et al., "Pharmacological characterization of the 6 Hz psychomotor seizure model of partial epilepsy," Epilepsy Research, 47:217-227 (2001).
Bell, J., "Treatment With CBD In Oily Solution Of Drug-Resistant Paediatric Epilepsies," Oct. 18, 2011, 3 pages; https://www.420magazine.com/community/threads/treatment-with-cbd-in-oily-solution-of-drug-resistant-paediatric-epilepsies. 154896/.
Ben-Ari, Y., "Seizures Beget Seizures: The Quest for GABA as a Key Player," Critical Reviews in Neurobiology, 18(1 -2): 135-144 (2006).
Bergamaschi, M.M., et al., "Safety and Side Effects of Cannabidiol, A Cannabis Sativa Constituent," Current Drug Safety, 2011, vol. 6(4), pp. 237-249.
Bhattacharyya, S. et al., Opposite Effects of delta-9-Tetrahydrocannabinol and Cannabidiol on Human Brain Function and Psychopathology, Neuropsychopharmacology, 35:764-774 (2010).
Bialer, M. & White, S., "Key factors in the discovery and development of new antiepileptic drugs," Nat Rev Drug Discov, 9(1):68-82 (2010); doi: 10.1038/nrd2997.
Bienenstock, D., "A Comprehensive History of Marijuana's Epilepsy-Treating Compound, CBD," Jun. 2014, Vice Article, retrieved from https://www.vice.com/da/article/mv53yp/desperately-seeking-cbd, 17 pages.
Bijnsdorp, I. V. et al., "Analysis of Drug Interactions," Chapter 34, Cancer Cell Culture, Methods in Molecular Biology, Second Edition, Ian A. Cree, Ed., 2011:731:421-34,19 pages.
Booth, "Legalization's opening of medical pot research is dream and nightmare," Denver Post, Dec. 14, 2013, http://www.denverpost.com/ci_24726291/legalizations-opening-medical-pot-research-is-dream-and, 6 pages.
Bowman et al., "Epilepsy," Encyclopedia of Life Sciences, 1, 2001; www.els.net, 8 pages.
Bromfield, E. B., Cavazos, J. 1., Sirven (Ed.,), An Introduction to Epilepsy [Internet], West Hartford, CT, American Epilepsy Society; 2006, PMID: 20821849, 187 pages.
Brown et al., Child Neurology Foundation, "LGS" (Lennox-Gastaut Syndrome), available at http://www.childneurologyfoundation.org/disorders/lgs-lennox-gastaut-syndrome, 2019, 7 pages.
Camfield, "Definition and natural history of Lennox-Gastaut Syndrome," Epilepsia, 52:3-9 (2011).
Campos-Castello, "Rational approach to treatment options for Lennox-Gastaut syndrome," Orphanet, Mar. 2003; https://www.orpha.net/data/patho/GB/uk-Lennox.pdf, 5 pages.
Capal, J. K. & Franz, D. N., "Profile of everolimus in the treatment of tuberous sclerosis complex: an evidence-based review of its place in therapy," Neuropsychiatric Disease and Treatment, 12:2165-2172 (2016).
Carlini, E. A et al., "Anticonvulsant Activity of Four Oxygenated Cannabidiol Derivatives," Research Communications in Chemical Pathology and Pharmacology, 12(1), Sep. 1975,15 pages.
Carlini, E. A. et al., "Letter: Cannabidiol and Cannabis sativa extract protect mice and rats against convulsive agents," J Pharm Pharmacol. Aug. 1973;25(8):664-5. doi: 10.1111/j.2042-7158.1973.tb10660.x.
Carvill, G.L. et al., "GABRA 1 and STXBP1: Novel Generic Causes of Dravet Syndrome," Neurology, 2014, vol. 82(14), pp. 1245-1253.
cdc.gov [online], "2 to 20 years: Girls Stature-for-age and Weight-for-age percentiles," National Center for Health Statistics and National Center for Chronic Disease Prevention and Health Promotion, last modified Nov. 2000, https://www.cdc.gov/growthcharts/data/set1clinical/cj411022.pdf, 1 page.
Charlotte's Web [ online], "Whole-Plant Cannabinoids Outperform Single Molecule Compounds," CWHemp.com, Jan. 11, 2017, retrieved on Jun. 16, 2017, URL https://www.cwhemp.com/blog/whole-plant-cw-hemp-cannabinoids, 6 pages.
Charlotte's Web [online], "When to expect Results from CW Hemp Oil," Mar. 13, 2017, retrieved on May 21, 2018, URL https://www.cwhemp.com/blog/expecting-results-from-hemp, 6 pages.
Chesney et al., "Adverse effects of cannabidiol: a systematic review and meta-analysis of randomized clinical trials," Neuropsychopharmacol., 45:1799-1806 (2020); https://doi.org/10.1038/s41386-020-0667-2.
ChildNeurologyFoundation.org [online], "Disorder Directory: Learn from the Experts—LGS (Lennon-Gastaut Syndrome)," Child Neurology Foundation, available on or before Sep. 6, 2015, retrieved on May 21, 2018; URL http://www.childneurologyfoundation.org/disorders/ lgs-Lennox-gastaut-syndrome, 10 pages.
Chiron, C. & Dulac, O., "The Pharmacologic Treatment of Dravet Syndrome," Epilepsia, 52 (Suppl. 2):72-75 (2011).
Chiron, S., "Stiripentol for the Treatment of Dravet Syndrome," Orphan Drugs: Research and Reviews, 2014, vol. 4, pp. 29-38.
Chiu, P. et al., "The Influence of Cannabidiol and A-Tetrahydrocannabinol on Cobalt Epilepsy in Rats," Epilepsia, 20:365-375 (1979).
Cholongitas, E. et al., "Systematic review: the model for end-stage liver disease—should it replace Child-Pugh's classification for assessing prognosis in cirrhosis?," Aliment Pharmacol Ther, 22:1079-1089 (2005).
Chou, T-C., "Drug combination studies and their synergy quantification using the Chou-Talalay method", Cancer Research (2010); 70(2): 440-446.
Chou, "Theoretical basis, experimental design, and computerized simulation of synergism and antagonism in drug combination studies," Pharmacol Rev, 58(3):621-681 (2006).
Christians, U. et al., "Biomarkers of Immunosuppressant Organ Toxicity after Transplantation- Status, Concepts and Misconceptions," Expert Opin Drug Metab Toxicol., 7(2): 175-200 (2011).
Chu-Shore, C. J. et al., "The natural history of epilepsy in tuberous sclerosis complex," Epilepsia, 51 (7): 1236-1241, 2010; doi: 10.1111/j. 1528-1167.2009.02474.
Ciccone, "Drop Seizure Frequency in Lennox-Gastaut Decrease With Cannabidiol," Neurology Advisor, Apr. 26, 2017; retrieved from the Internet: URL:https://neurologyadvisor.com/aan-2017-coverage/aan-2017-cannabidiol-reduces-drop-seizures-in-lennox-gasaut-syndrome/article/652931, 6 pages.
Cilio, Maria Roberta, M.D., Ph.D. of the Pediatric Epilepsy and Clinical Neurophysiology for the University of California, San Francisco presents her talk on "CBD in Children with Treatment-Resistant Epilepsies: Planned Trials in Dravet and Lennox-Gastaut Syndromes," at NYU School of Medicine's Cannabidiol Conference (Oct. 4, 2013). Video published online. http://faces.med.nyu.edu/research-education/cannabidiol-conference, 44 pages.
Cilio, M.R., et al., "The Case for Assessing Cannabidiol in Epilepsy," Epilepsia, 2014, vol. 55(6), pp. 787-790.

(56) References Cited

OTHER PUBLICATIONS

Ciszek M., "Once- Versus Twice-daily Tacrolimus: Are the Formulations Equivalent?" Central European Journal of Urology, 2013;66(3):350-351.
Citti et al., "Journal of Pharmaceutical and Biomedical Analysis", vol. 175, 2019, 112752, ISSN 0731-7085, (Year: 2019).
Citti et al., "Pharmaceutical and biomedical analysis of cannabinoids: A critical review," Journal of Biopharmaceutical and Biomedical Analysis, 147:565-579 (2018).
ClinicaiTrials.gov archive, History of Changes for Study: NCT02324673, National Institute of Health U.S. National Library of Medicine (Dec. 19, 2014), https://classic.clinicaltrials.gov/ct2/history/NCT02324673?V 1=View#StudyPageTop, 13 pages.
clinical trials.gov [online], Identifier: NCT02006628, A study to compare the change in symptom severity in participants with schizophrenia or related psychotic disorderwhen treated with GWP42003 or placebo in conjunction with existing anti-psychotic therapy over a period of six weeks, Jazz Pharmaceuticals, U.S. National Library of Medicine, last update posted Sep. 28, 2022, 9 pages; Retrieved from https://clinicaltrials.gov/ct2/show/NCT02006628.
Clinical trials.gov [online], Identifier: NCT02091206, A Dose Ranging Pharmacokinetics and Safety Study of GWP42003-P in Children With Dravet Syndrome (GWPCARE1), Jazz Pharmaceuticals, U.S. National Library of Medicine, last update posted Sep. 28, 2022, 9 pages; Retrieved from https://clinicaltrials.gov/ct2/show/NCT02091206.
Clinical trials.gov [online], Identifier: NCT02091375, Antiepileptic Efficacy Study of GWP42003-P in Children and Young Adults WithDravet Syndrome (GWPCARE1), Jazz Pharmaceuticals, U.S. National Library of Medicine, last update posted Sep. 28, 2022, 40 pages; Retrieved from https://www.clinicaltrials.gov/ct2/show/NCT02091375.
Clinical trials.gov [online], Identifier: NCT02224690, A Study to Investigate the Efficacy and Safety of Cannabidiol (GWP42003-P; CBD) as Adjunctive Treatment for Seizures Associated With Lennox-Gastaut last https://clinicaltrials.qov/ct2/show/NCT02224690. update posted Sep. 8, 2022, 3 pages; Retrieved fromSyndrome in Children and Adults (GWPCARE4) Jazz Pharmaceuticals, U.S. National Library of Medicine.
Collins, T.R., "What Neurologists are Doing About Medical Marijuana?," Neurology Today, Apr. 17, 2014, vol. 4(8), 8 pages.
Combined Search and Examination Report mailed Jan. 4, 2012 for Application No. GB 1116789.7, 8 pages.
Combined Search and Examination Report mailed Mar. 25, 2011 for Application No. GB 1100043.7, 8 pages.
Combined Search and Examination Report mailed Sep. 5, 2014 for Application No. GB 1414813.4, 8 pages.
Combined Search and Examination Report Under Sections 17 and 18 (3) for International Application No. GB 1418166.3, dated Jul. 2, 2015, 8 pages.
Combined Search and Examination Report Under Sections 17 and 18 (3) for International Application No. GB 1418170.5, dated Jul. 2, 2015, 6 pages.
Combined Search and Examination Report Under Sections 17 and 18 (3) for International Application No. GB 1418171.3, dated Jun. 29, 2015, 8 pages.
Combined Search and Examination Report Under Sections 17 and 18 (3) for International Application No. GB 1506550.1, dated Feb. 5, 2016, 9 pages.
Combined Search and Examination Report Under Sections 17 and 18 (3) for International Application No. GB1121919.3, dated Feb. 29, 2012, 8 pages.
Combined Search and Examination Report Under Sections 17 and 18 (3) for International Application No. GB1410771.8, dated Feb. 27, 2018, 7 pages.
Communication of a Notice of Opposition for Application No. 107342541.5 dated Dec. 17, 2014, 1 page.
Communication Pursuant to Article 94(3) EPC in European Patent Application No. 10734541.5, dated Oct. 23, 2012, 3 pages.
Conry et al., "Clobazam in the treatment of Lennox-Gastaut syndrome," Epilepsia, 50:1158-1166 (2009).
Consroe et al. "Anticonvulsant drug antagonism of delta9tetrahydrocannabinol-induced seizures in rabbits," Res Commun Chem Pathol Pharmacol., 16(1):1-13 (1977).
Consroe et al. "Anticonvulsant interaction of cannabidiol and ethosuximide in rats," J Pharm Pharmacol., 29(8):500-501 (1977). doi: 10.1111/j.2042-7158.1977.tb11378.x.
Consroe et al. "Anticonvulsant nature of marihuana smoking," JAMA, 234(3):306-307 (1975).
Consroe et al., "Assay of Plasma Cannabidol by Capillary Gas Chromatography/ion Trap Mass Spectroscopy Following High-Dose Repeated Daily Oral Administration in Humans," Pharmacology Biochemistry & Behavior, 40:517-522 (1991).
Consroe, et al. "Cannabidiol—antiepileptic drug comparisons and interactions in experimentally induced seizures in rats." J Pharmacol Exp Ther. Apr. 1977;201(1):26-32.
Consroe et al. Chapter 12, "Potential Role of Cannabinoids for Therapy of Neurological Disorders," in Marijuana Cannabinoids: Neurobiology and Neurophysiology, Ed. L. Murphy (1992), 72 pages.
Consroe et al.,. "Chapter 2: Therapeutic Potential of Cannabinoids in Neurological Disorders," Cannabonioids as Therapeutic Agents, R. Mechoulam, Ed., 1986, pp. 21-49.
Consroe et al., "Controlled clinical trial of cannabidiol in Huntington's Disease," Pharmacology Biochemistry & Behavior, 40:701-708 (1991).
Consroe et al., "Effects of cannabidiol on behavioral seizures caused by convulsant drugs or current in mice," Eur J Pharmacol., 83(3-4):293-298 (1982).
Consroe, P. et al. (1981) Antiepileptic Potential of Cannabidol Analogs. J Clin Pharmacol, 21 :428S-436S.
Consroe, P., et al.; "Open label evaluation of cannabidiol in dystonic movement disorders," International Journal of Neuroscience. (Jan. 1, 1986); 30(4):277-282.
Costa, B. et al., "Oral anti-inflammatory activity of cannabidiol, a non-psychoactive constituent of cannabis, in acute carrageenan-induced inflammation in the rat paw," Naunyn-Schmiedeberg's Arch Pharmacal, 369:294-299 (2004).
Cotter, B., "Medicinal marijuana stops seizures, brings hope to little girl," The Gazette, Jun. 9, 2013, 8 pages; https://gazette.com/health/medicinal-marijuana-stops-seizures-brings-hope-to-a-little- girl/article_520b074e-5c46-5d75-af95-bdd060f4a8b9.html.
Cotterell, A., "How One Young Girl Could Change Idaho's Strict Marijuana Laws," Jun. 17, 2014; https://www.knkx.org/law/2014-06-19/how-one-young-girl-could-change-idahos-strict-marijuana-laws, 8 pages.
Crespel et al., "Lennox-Gastaut Syndrome," Chapter 14, in Epileptic Syndromes in Infancy, Childhood, and Adolescence, 5th Edition, ed. M. Bureau, et al., pp. 189-216.
Crowther et al., "The Medication of Cannabis," The transcript of a Witness Seminar held by the Wellcome Trust Centre for the History of Medicine at UCL, London, on Mar. 24, 2009; http:/lqmro.qmul.ac.uk/xmlui/handle/123456789/2822, 90 pages.
Crumrine, P.K., "Management of Seizures in Lennox-Gastaut Syndrome," Pediatric Drugs, 2011, vol. 13(2), pp. 107-118.
Cunha et al., "Chronic Administration of Cannabidiol to Healthy Volunteers and Epileptic Patients," Pharmacology, 21:175-185 (1980).
Curatolo, P. et al., "Management of epilepsy associated with tuberous sclerosis complex (TSC): Clinical recommendations," European Journal of Paediatric Neurology, 16:582-586 (2012).
De Deyn et al., "Chemical models of epilepsy with some reference to their applicability in the development of anticonvulsants," Epilepsy Research, 12:87-110 (1992).
De Meijer, E., "The Chemical Phenotypes (Chemotypes) of Cannabis," Chapter 5, Handbook of Cannabis, Roger G. Pertwee (Ed.), pp. 89-110 (2014).
Decision in IPR2017 -00503 dated Jul. 7, 2017, 26 pages.
Decision in Opposition Proceedings (Art. 101(3)(a) and 106(2) EPC in European Patent Application No. EP2448637, dated Dec. 15, 2016, 91 pages.

(56) References Cited

OTHER PUBLICATIONS

Depakene (valproic acid) capsules and oral solution, CV, Prescribing Information, 1978, 54 pages; https://www.accessdata.fda.gov/drugsatfda_docs/label/2013/018081s056lbl.pdf.
DeRosa et al., "Chapter XI: Epilepsy," Significant Pharmaceuticals Reported in US Patents, 1st Edition, May 2007,10 pages.
Devarbhavi, "An update on drug-induced liver injury," J. Clinical and Experimental Hepatology, 2(3):247-259 (2012).
Devinsky et al., "Cannabidiol (CBD) significantly reduces drop seizure frequency in Lennox-Gastaut syndrome (LGS): results of a dose-ranging, multi-center, randomized, double-blind, placebo-controlled trial (GWPCARE3)," Epilepsia, 58:S13-S14 (2017).
Devinsky et al., "Cannabidiol efficacy independent of clobazam: Meta-analysis of four randomized controlled trials," Acta Neurol Scand., 142:531-540 (2020).
Devinsky, et al., "Cannabidiol: Pharmacology and potential therapeutic role in epilepsy and other neuropsychiatric disorders," Epilepsia, Jun. 2014, 55(6), 791-802.
Devinsky et al., "Efficacy and safety of Epidiolex (cannabidiol) in children and young adults with treatment-resistant epilepsy: Initial data from expanded access program," Jan. 2015, 2 pages.
Devinsky et al., "Epidiolex (Cannabidiol) in Treatment Resistant Epilepsy," Apr. 2015; https://epilepsyontario.org/wp-content/uploads/2015/Epidiolex-Cannabidiol-in-Treatment-Resistant-Epilepsy AAN-POSTER 08Apr2015.pdf, 1 page.
Devinsky et al., Trial Protocol, Supplementary Material to "Trial of Cannabidiol for Drug-Resistant Seizures in the Dravet Syndrome," N Engl J Med, 376(21 ):2011-2020 (2017), 426 pages.
Devinsky, O. et al., "Cannabidiol in patients with treatment-resistant epilepsy: an open-label interventional trial," The Lancet Neurology, Published online; Dec. 23, 2015; 9 pages; doi:https://doi.org/10.1016/S1474-4422(15)00379-8.
Devinsky, O. et al., "Trial of Cannabidiol for Drug-Resistant Seizures in the Dravet Syndrome," N Engl J Med, 376(21):2011-2020 (2017).
Devinsky, Orrin, M.D. of the Department of Neurology for NYU Langone School of Medicine presents his talk on "Cannabidiols: A Brief History," at NYU School of Medicine's Cannabidiol Conference (Oct. 4, 2013). Video published online. http://faces.med.nyu.edu/research-education/cannabidiol-conference, 16 pages.
Di Marzo, Vincenzo, Ph.D. of the Endocannabinoid Research Group Istituto di Chimica Biomolecolare, Consiglio Nazionale delle Ricerche, Pozzuoli, Napoli, Italy presents his talk on "Cannabinoid Pharmacology & Mechanism of Action," at NYU School of Medicine's Cannabidiol Conference (Oct. 4, 2013). Video published online. http://faces.med.nyu.edu/research-education/cannabidiol-conference, 32 pages.
Diacomipm Product Monograph, Submission Control 142417, Date of Preparation, Dec. 19, 2012, 37 pages.
Dilantin-125@, NDA 08762 Dilantin-125 (Phenytoin Oral Suspension, USP) FDA Approved Labeling Text dated Feb. 2013, 15 pages.
DiMarzo, V., Declaration Under 37 C.F.R. 1.132, dated Aug. 24, 2017, 21 pages.
Dos Santos, R. G. et al., "Phytocannabinoids and epilepsy," Journal of Clinical Pharmacy and Therapeutics, 40:135-143 (2015).
Dravet, "The core Dravet syndrome phenotype," Epilepsia, 52 Suppl 2:3-9 (2011); doi: 10.1111/j.1528- 1167.2011.02994.x.
Dreifus, et al., "Proposal for Revised Clinical and Electroencephalographic Classification of Epileptic Seizures," Epilepsie., 22:489-501 (1981).
Ebrahimi-Fakhari, D. et al., "Cannabidiol Elevates mTOR Inhibitor Levels In Tuberous Sclerosis Complex Patients," (2020) Pediatric Neurology, 12 pages; https://doi.org/10.1016/j.pediatrneurol.2019.11.017.
Elsohly and Gul, "Constituents of Cannabis Sariva," Chapter 1, Handbook of Cannabis, ed. Roger G. Pertwee, pp. 3-22 (2014).
Elsohly, M.A., et al., "Chemical Constituents of Marijuana: the Complex Mixture of Natural Cannabinoids," Life sciences, Dec. 22, 2005, vol. 78(5), pp. 539-548.
Engel, Chapter 1, "What Should be Modeled," In Models Seizure Epilepsy, 2006, 14 pages.
Engel, "Report of the ILAE classification core group," Epilepsia, 47(9):1558-1568 (2006).
EP Third Party Observations for Application No. EP10734541.5, mailed Apr. 3, 2017, 19 pages.
EP Third Party Observations for Application No. EP11712658.1, dated Nov. 22, 2013, 14 pages.
Epidiolex® (cannabidiol) oral solution, CV, Prescribing Information, 2018, 30 pages; https://www.accessdata.fda.gov/drugsatfda_docs/label/2018/210365lbl.pdf.
Epidiolex (cannabidiol) oral solution, CV, Prescribing Information, 2021, 38 pages; https://www.accessdata.fda.gov/drugsatfda_docs/label/2021/210365rig1s011lbl.pdf.
Epidiolex (cannabidiol) oral solution, CV, Prescribing Information, 2024, 32 pages; https://pp.jazzpharma.com/pi/epidiolex.en.USPI.pdf.
Epidyolex 100 mg oral solution, Summary of Product Characteristics, European Medicines Compendium, Sep. 2019, 19 pages; https://web.archive.Org/web/20200920022105/https://www.medicines.org.uk/emc/product/10781/smpc.
Epilepsy Patients Flock to Colorado after Medical Pot Gives Them Hope, Nov. 18, 2013, CBS Colorado News, 4 pages.
EPO Annex to the Communication in Opposition for European Patent No. 10734541.5, dated Jan. 28, 2016, 5 pages.
EPO Notice of Appeal in European Patent Application No. EP2448637, dated Feb. 14, 2017, 5 pages.
EPO Notice of Opposition to a European Patent No. EP2448637, dated Dec. 5, 2014, 20 pages.
EPO Opponent Response to the Preliminary Opinion of the Opposition Division in European Patent No. EP2448637, dated Jun. 23, 2016, 27 pages.
EPO Opponent Response to the Written Submissions in European Patent No. EP2448637, dated Nov. 4, 2016, 3 pages.
EPO Opponent Response to the Written Submissions in European Patent No. EP2448637, dated Oct. 12, 2016, 18 pages.
EPO Opponent Response to the Written Submissions in European Patent No. EP2448637, dated Oct. 20, 2016, 3 pages.
EPO Opposition, Expert Statement of Professor Anthony G. Marson in European Application No. EP10734541.5, dated Jun. 14, 2016, 9 pages.
EPO Opposition, Expert Statement of Professor Benjamin J. Whalley in European Application No. EP10734541.5, dated Sep. 9, 2016, 11 pages.
EPO Opposition, Expert Statement of Vincenzo Di Marzo in European Application No. EP10734541.5, dated Sep. 9, 2016, 10 pages.
EPO Reply of the Patent Proprietor to the Notice(s) of Opposition in European Patent No. 2448637, dated May 28, 2015, 12 pages.
EPO Reply to Opponent's Written Submission in European Patent No. EP2448637, dated Nov. 4, 2016, 13 pages.
EPO Reply to Opponent's Written Submission in European Patent No. EP2448637, dated Oct. 18, 2016, 5 pages.
EPO Reply to Preliminary Opinion and Opponent's Observations in European Patent No. EP2448637, dated Sep. 9, 2016, 65 pages.
Evans, Randolph W., Neurology Case Studies, Neural Clin 24, xi-xii, 2006, 2 pages.
Ex parte Edelstam, Appeal No. 2016/006358, mail date Jun. 21, 2017 (Year: 2017), 5 pages.
Ex parte Miller, Appeal 2009-011751, mail date Jul. 8, 2010 (Year: 2010), 23 pages.
Examination Report mailed Mar. 18, 2014 for Application No. GB1100043.7, 3 pages.
Fabiano, V. et al., "Adverse drug reactions in newborns, infants and toddlers: pediatric pharmacovigilance between present and future," Expert Opinion on Drug Safety, 11(1): 95-105 (2011); doi:10.1517/14740338.2011.584531.
FDA Good Review Practice: Clinical Review of Investigational New Drug Applications, Office of New Drugs in the Center for Drug Evaluation and Research at the Food and Drug Administration, Dec. 2013, 113 pages.

(56) References Cited

OTHER PUBLICATIONS

FDA Guidance for Industry: Botanical Drug Development, U.S. Dept. of Health and Human Services: Food and Drug Administration, Dec. 2016, 34 pages.
FDA Guidance for Industry on Drug-Induced Liver Injury: Premarketing Clinical Evaluation, Food and Drug Administration, Jul. 30, 2009, 4 pages.
FDA Guidance for Industry: Q11 Development and Manufacture of Drug Substances, U.S. Dept. of Health and Human Services: Food and Drug Administration, Nov. 2012, 36 pages.
FDA'S Guidance for Industry Q3A Impurities in New Drug Substances, Revision 2, Jun. 2008, 17 pages.
FDA Guideline for Submitting Supporting Documentation in Drug Applications for the Manufacture of Drug Substances, published in 1987, 20 pages.
Feierman, D. E. & Lasker, J. M., "Metabolism of fentanyl, a synthetic opioid analgesic, by human liver microsomes. Role of CYP3A4," Drug Metabolism and Disposition, 24(9):932-939, Sep. 1996, Abstract. https://dmd.aspetjournals.Org/content/24/9/932, 4 pages.
Fernandez-Ruiz, J. et al., "Cannabidiol for neurodegenerative disorders: important new clinical applications for this phytocannabinoid?" British Journal of Pharmacology, 75(2):323-333 (2012).
Flatow, N "How Medical Marijuana Is Giving a Six-Year-Old Boy New Life," Sep. 18, 2012, 2 pages;https://archive.thinkprogress.org/how-medical-marijuana-is-giving-a-six-year-old-boy-new-life-b5a486fbid48/.
French, J. A. et al., "Adjunctive everolimus therapy for treatment-resistant focal-onset seizures associated with tuberculosis sclerosis (EXIST-3): a phase 3, randomised, double-blind, placebo-controlled study," Lancet, 388:2153-2163 (2016).
French, Jacqueline A., M.D. Professor of Neurology at the NYU Epilepsy Center presents her talk on "Trials for Disease Modifying Therapies in Epilepsy," at NYU School of Medicine's Cannabidiol Conference (Oct. 4, 2013). Video published online. http://faces.med.nyu.edu/research-education/cannabidiol-conference, 22 pages.
Friedman, Daniel, M.D. Assistant Professor of Neurology at the NYU Comprehensive Epilepsy Center presents his talk on "Pharmacology of CBD in Humans," at NYU School of Medicine's Cannabidiol Conference (Oct. 4, 2013). Video published online. http://faces.med.nyu.edu/research-education/cannabidiol-conference, 14 pages.
Fryar, C. D. et al., Anthropometric reference data for children and adults: United States, 2011-2014, National Center for Health Statistics. Vital Health Statistics, 3(39), 2016, 46 pages.
Gaber, O. et al., "Conversion from Twice-daily Tacrolimus Capsuled to Once Daily Extended Release Tacrolimus(LCPT): a Phase 2 Trial of Stable Renel Transplant Recipients," Clinical and Translational Research, vol. (96), No. 2, 191-197, 2013.
Galetin et al., "Multisite Kinetic Analysis of Interactions Between Prototypical CYP3A4 Subgroup Substrates: Midazolam, Testosterone, and Nifedipine," Drug Metabolism and Disposition, 31(9):1108-1116 (2003).
Gallily, R. et al., Overcoming the Bell-Shaped Dose-Response of Cannabidiol by Using Cannabis Extract Enriched in Cannabidiol, Pharmacology & Pharmacy, 2015, 6, 75-85, Published Online Feb. 2015 in SciRes. http://www.scirp.org/journal/pp, http://dx.doi.org/10.4236/pp.2015.62010.
Gaoni, Y. & Mechoulam, R., "Isolation, Structure, and Partial Synthesis of an Active Constituent of Hashish," J. Am. Chem. Soc. 1964, 86, 8, 1646-1647.
Gaoni, Y. & Mechoulam, R., "The Isolation and Structure of A1-Tetrahydrocannabinol and Other Neutral Cannabinoids from Hashish," J Am Chem Soc. Jan. 13, 1971;93(1):217-24. doi: 10.1021/ja00730a036.
Garde, D., "GW Pharmaceuticals Announces Physician Reports of Epidiolex Treatment Effect in Children and Young Adults With Treatment-Resistant Epilepsy From Physician-Led Expanded Access Treatment Program," Jun. 17, 2014, 4 pages; https://www.fiercebiotech.com/biotech/gw-pharmaceuticals-announces- physician-reports-of-epidiolex-r-treatment-effect-children-and.
Garde, "GW Pharma—GW Pharmaceuticals Announces New Physician Reports of Epidiolex® Treatment Effect in Children and Young Adults With Treatment-Resistant Epilepsy," Oct. 14, 2014; https://ir.gwpharm.com/news-releases/news-release-details/gw-pharmaceuticals-announces-new-physician-reports-epidiolexr-0, 4 pages.
Gardner, "Cannabidiols: Potential Use in Epilepsy & Other Neurological Disorders," Cannabidiol Conference at NYU School of Medicine, Oct. 2013. NYU Langone Health. Retrieved from the Internet Nov. 2019. URL: http://faces.med.nyu.edu/research-education/cannabidiol-conference, 4 pages.
Gardner [online], "Comes Now Epidiolex (FDA Approves IND Studies of CBD)," BeyondTHC.com, Oct. 22, 2013, retrieved on Jan. 31, 2018, http://www.beyondthc.com/comes-now-epidiolex-fda- approves-ind-studies-of-cbd, 4 pages.
Gaston, T. E. et al., "Cannabis for the Treatment of Epilepsy: an Update," Curr Neurol Neurosci Rep., 18(11):73 (2018), 9 pages; doi: 10.1007/s11910-018-0882-y.
Gaston, T. E. et al., "Quality of life in adults enrolled in an open-label study of cannabidiol (CBD) for treatment-resistant epilepsy," Epilepsy & Behavior, 95:10-17 (2019).
Gauthier et al., "Clobazam: A Safe, Efficacious, and Newly Rediscovered Therapeutic for Epilepsy," CNS Neurosci Ther., 21 (7):543-548 (2015); doi: 10.1111/cns. 12399. Epub Apr. 28, 2015.
Gedde et al., "Whole Cannabis Extract of High Concentration Cannabidiol May Calm Seizures in Highly Refractory Pediatric Epilepsies," American Epilepsy Society, Dec. 2013, pp. 449-1450. Abstract.
Gedde M., et al., "Whole Cannabis Extract of High Concentration Cannabidiol May Calm Seizures in Highly Refractory Pediatric Epilepsies," American Epilepsy Society, Dec. 2013, pp. 449-450.
Gedde, Retrospective Case Review of High CBD, Low THC Cannabis Extract (Realm Oil) for Intractable Seizure Disorders, 2013 Realm of Caring Foundation, 4 pages.
Geffrey et al. "Cannabidiol (CBD) Treatment for Refractory Epilepsy," American Epilepsy Society, Annual Meeting Abstract 2.427, 2014, retrieved on Feb. 10, 2017, URL https://www.aesnet.org/meetings_events/annual_meeting_abstracts/view/1868979, 2 pages.
Geffrey et al., "Cannabidiol (CBD) Treatment for Refractory Epilepsy in Tuberous Sclerosis Complex," American Epilepsy Society, Annual General Meeting, Abstract, accessed on Jun. 23, 2015; https://www.aesnet.org/meetings_events/annual_meeting_abstracts/view/1868979, 2 pages.
Geffrey et al., "Drug-drug interaction between clobazam and cannabidiol in children with refractory epilepsy," Epilepsia, 56(8):1246-1251 (2015).
Gemmill, R. M. et al., "Synergistic growth inhibition by Iressa and Rapaymycin is modulated by VHL mutations in renal cell carcinoma," British Journal of Cancer, 92:2266-2277 (2005).
Geode & Maa, "Whole Cannabis Extract of High Concentration Cannabidiol May Calm Seizures in HighlyRefractory Pediatric Epilepsies," American Epilepsy Society, 67th Annual Meeting, Dec. 6-10, 2013. Abstract.
Gillen, D., "How Does Caffeine Affect CBD?", Apr. 21, 2019, available at: https://web.archive.org/web/20191220210719/https://greendoorcbd.com/blogs/news/how-does-caffeine- affect-cbd, 4 pages.
Gloss et al., "Cannabinoids for epilepsy," Cochrane Databse Syst Rev. Mar. 5, 2014;(3):CD009270/14651858.CD009270.pub3, 9 pages.
Goldenberg, M. M., "Overview of Drugs Used For Epilepsy and Seizures," P & T, 35(7):392-415 (2010).
Goodman & Gilman, The Pharmacological Basis of Therapeutics (Brunton, Laurence L.; Lazo, John S.; Parker, Keith, eds. (2006); New York: McGraw-Hill. ISBN 0-07-142280-3); Chapter 19, Pharmacotherapy of the Epilepsies, 28 pages.
Greaves et al., "First Dose of Potential New Medicines to Humans: How Animals Help," Nature Reviews Drug Discovery, 3:226-236 (2004).
Green Roads CBD Coffee and Tea, Product Page, 2023, 5 pages; https://greenroads.com/collections/cbd- tea-cbd-coffee?nfsn=2488702.aa938d.

(56) References Cited

OTHER PUBLICATIONS

Gresham et al. "Treating Lennox-Gastaut syndrome in epileptic pediatric patients with third generation rufinamide," Neuropsychiatr Dis Treat., 6:639-645, Oct. 5, 2010.
Grotenhermen et al., "The therapeutic potential of cannabis and cannabinoids", Dtsch Arztebl Int., vol. 109, No. 29-30, pp. 495-501, 2012.
Guerrini, et al., "Lamotrigine and Seizure Aggravation in Severe Myoclonic Epilepsy," Epilepsia, 39(5):508-512 (1998).
Guimares, et al., "Antianxiety effect of cannabidiol in the elevated plus-maze," Psychopharmacology (Berl)., 100(4):558-9 (1990); doi: 10.1007/BF02244012.
Gunning et al., "Cannabidiol in conjunction with clobazam: analysis of four randomized controlled trials," Acta Neurol Scand., 143:154-163 (2021).
Gupta, S., "Why I changed my mind on weed," Aug. 8, 2013; https://www.cnn.com/2013/08/08/health/gupta-changed-mind-marijuana/index.html, 8 pages.
Gupta Video 2013, Weed—CNN Special; https://www.youtube.com/watch?v=Z31Mfi1_K6U, no page Nos. available.
GWPharm [online], "GW Pharmaceuticals Announces Epidiolex(R) Receives Fast Track Designation from FDA for the Treatment of Dravet Syndrome," GW Pharmaceuticals Press Release, Jun. 6, 2014, retrieved on Mar. 1, 2017, 2 pages; URL https://www.gwpharm.com/about-us/news/gw-pharmaceuticals-announces-epidiolex%C2%AE-receives-fast-track-designation-fda-treatment.
GWPharm [online], "GW Pharmaceuticals Provides Update on Orphan Program in Childhood Epilepsy for Epidiolex ®," GW Pharmaceuticals Press Release, Nov. 15, 2013, 5 pages.
GWPharm [online], "GW Pharmaceuticals Receives Orphan Drug Designation by FDA for Epidiolex® in the treatment of Lennox-Gastaut Syndrome," GW Pharmaceuticals Press Release, Feb. 28, 2014, retrieved on Feb. 10, 2017, URL https://www.gwpharm.com/about-us/news/gw-pharmaceuticals-receives-orphan-drug-designation-fda-epidiolex%C2%AE-treatment-lennox, 4 pages.
Ha et al., "Epilepsy: Treatment and Management," US Pharm., 38(1):35-39 (2013).
Haller, S. & Carroll, I., "Medical marijuana for kids Some praise results while others worry about risks," Jul. 9, 2013, 3 pages; https://www.nbcnews.com/healthmain/medical-marijuana-kids-some-praise-results- whi le-others-worry-abou t-6c10506407.
Hancock, E. C. & Cross, J. H., "Treatment of Lennox-Gastaut syndrome (Review)," Cochrane Database of Systematic Reviews, 2013, Issue 2. Art. No. CD003277, doi: 10.1002/14651858.CD003277.pub3., 35 pages.
Hanus, et al., "Phytocannabinoids: a unified critical inventory," Nat Prod Rep. Nov. 23, 2016; 33(12):1357-1392.
Hauser, N. et al., "High on Cannabis and Calcineurin Inhibitors: A Word of Warning in an Era of Legalized Marijuana," Hindawi Publishing Corporation, Case Reports In Transplantation, vol. 2016, Sep. 6, 2018;2018:7095846. doi: 10.1155/2018/7095846. eCollection 2018, 4 pages.
Hazenkamp, A., "Cannabis; extracting the medicine," Doctoral Thesis, 1976, Proefschrift Universiteit Leiden;https://extractionmagazine.com/wp-contenVuploads/2018/06/Cannabis-extracting-the-medicine-Arno- Hazekamp-Thesis.pdf, 187 pages.
Hazenkamp, A. et al., "Quantitative Analysis of Cannabinoids from Cannabis sativa Using H-NMR," Chem. Pharm. Bull., 52(6):718-721 (2004).
Hefler, J., "Parents of epileptic N.J. tot lament medical marijuana delays," The Philadelphia Enquirer, Jun. 22, 2013, 5 pages; https://www.inquirer.com/philly/health/20130623_Parents_of_epileptic_N_J tot_lament_medical_marijuana_delays.html.
Hegde, M. et al., "Seizure exacerbation in two patients with focal epilepsy following marijuana cessation," Epilepsy & Behavior, 25:563-566 (2012).
Herlopian, A. et al., "Cannabidiol in treatment of refractory epileptic spasms: An open label study," Epilepsy & Behavior, 106:106988 (2020), 7 pages; https://doi.org/10.1016/j.yebeh.2020.106988.

Hess, E. J. et al., "Cannabidiol as a new treatment for drug-resistant epilepsy in tuberous sclerosis complex," Epilepsia, 57(10):1617-1624 (2016); doi: 10.1111/epi.13499.
Hill, A. J. et al., "Phytocannabinoids as novel therapeutic agents in CNS disorders," Pharmacology & Therapeutics, 133:79-97 (2012).
Hill et al., "Cannabidivarin is anticonvulsant in mouse and rat," Br. J Pharmacol, 167(8):1629-1642 (2012).
Hillig, K. W. & Mahlberg, P. G., "A chemotaxonomic analysis of cannabinoid variation in Cannabis (Cannabaceae)," American Journal of Botany, 91 (6):966-975 (2004).
Holmes, G. L. et al., "Tuberous Sclerosis Complex and Epilepsy: Recent Developments and Future Challenges," Epilepsia, 48(4):617-630, 2007.
Hussain, S. A. et al., "Perceived efficacy of cannabidiol-enriched cannabis extracts for treatment of pediatric epilepsy: A potential role for infantile spasms and Lennox-Gastaut syndrome," Epilepsy & Behavior, 47:138-141 (2015).
ICE Epilepsy Alliance, the Dravet Syndrome Spectrum, Nov. 2, 2008, 2 pages.
Ilegal Trailer, YouTube video, Mar. 27, 2014; https://www.youtube.com/watch?v=CtJJ1pzMKxs, 5 pages.
*Insys Development Company, Inc.* v. *GW Pharma Limited and Otsuka Pharmaceutical Co., Ltd.*, Declaration by Mark Polyakov, IPR2017-00503, U.S. Pat. No. 9,066,920, dated May 29, 2018, 1 page.
*Insys Development Company, Inc.* v. *GW Pharma Limited and Otsuka Pharmaceutical Co., Ltd.*, Final Written Decision in IPR2017-00503, U.S. Pat. No. 9,066,920, dated Jan. 3, 2019, 40 pages.
*Insys Development Company, Inc.* v. *GW Pharma Limited and Otsuka Pharmaceutical Co., Ltd.*, Petition for Inter Partes Review, IPR2017-00503, U.S. Pat. No. 9,066,920, dated Dec. 16, 2016, 78 pages.
*Insys Development Company, Inc.* v. *GW Pharma Limited and Otsuka Pharmaceutical Co., Ltd.*, Petitioner's Brief Regarding Ground III of the IPR, IPR2017-00503, U.S. Pat. No. 9,066,920, dated May 29, 2018, 45 pages.
*Insys Development Company, Inc.* v. *GW Pharma Limited and Otsuka Pharmaceutical Co., Ltd.*, Petitioner's Reply to patent Owner's Response, IPR2017-00503, U.S. Pat. No. 9,066,920, dated Jun. 19, 2018, 6 pages.
*Insys Development Company, Inc.* v. *GW Pharma Limited and Otsuka Pharmaceutical Co., Ltd.*, Petitioner's Reply to Response in IPR2017-00503, U.S. Pat. No. 9,066,920, dated Jan. 19, 2018, 36 pages.
Insys Therapeutics Commences Dosing in Phase 1/2 Safety and Pharmacokinetic Study of Cannabidiol Oral Solution in Pediatric Epilepsy Patients, BioSpace (Apr. 23, 2015); https://www.biospace.com/articlelreleases/insys-therapeutics-commencesdosing-in-phase-1-2-safety-and-pharmacokinetic-study-of-cannabidiol-oral-solution-in-pediatricepilepsy-patients-/, 3 pages.
Insys Therapeutics, Inc., Corporate Integrity Agreement and Conditional Exclusion Release, 2014, 100 pages.
Insys Therapeutics, Inc., Quarterly Report Form Q-10, U.S. Securities and Exchange Commission, Mar. 31, 2014; insy2014033110q.htm, 42 pages.
Insys Therapeutics Submits Drug Master File For Cannabidiol Active Pharmaceutical Ingredient (API), Marketwired, May 29, 2014; https://www.biospace.com/article/releases/insys-therapeutics-submits-drug- master-file-for-cannabidiol-active-pharmaceutical-ingredient-api-1, 5 pages.
International Preliminary Report on Patentability for Application No. PCT/GB2015/053030, dated Apr. 18, 2017, 6 pages.
International Preliminary Report on Patentability for International Application No. PCT/GB2010/051066, dated Jun. 9, 2011, 6 pages.
International Preliminary Report on Patentability for International Application No. PCT/GB2012/052284, dated Dec. 12, 2013.
International Preliminary Report on Patentability for International Application No. PCT/GB2012/052284, dated Mar. 29, 2014, 12 pages.
International Preliminary Report on Patentability in International Application No. PCT/GB2010/051066, dated May 3, 2011, 4 pages.

(56) References Cited

OTHER PUBLICATIONS

International Preliminary Report on Patentability mailed Sep. 1, 2017 for International Application No. PCT/GB2016/051792, 14 pages.
International Search Report and Written Opinion for International Application No. PCT/GB2011/050649, dated Sep. 30, 2012, 10 pages.
International Search Report and Written Opinion for International Application No. PCT/GB2015/051066, dated Jan. 1, 2012, 6 pages.
International Search Report and Written Opinion for International Application No. PCT/GB2015/051775, dated Dec. 23, 2015, 9 pages.
International Search Report and Written Opinion mailed Aug. 25, 2015 for International Application No. PCT/GB2015/051776, 11 pages.
International Search Report and Written Opinion mailed Aug. 26, 2015 for International Application No. PCT/GB2015/051775, 9 pages.
International Search Report and Written Opinion mailed Dec. 13, 2010 for International Application No. PCT/GB2010/051066, 3 pages.
International Search Report and Written Opinion mailed May 30, 2011 for Application No. PCT/GB2011/050649, 15 pages.
International Search Report and Written Opinion mailed Nov. 16, 2012 for International Application No. PCT/GB2012/052284, dated Mar. 29, 2014, 12 pages.
International Search Report for International Application No. PCT/GB2010/051066, dated Jan. 6, 2011, 4 pages.
International Search Report for International Application No. PCT/GB2012/050002, dated Feb. 24, 2012, 10 pages.
International Search Report for International Application No. PCT/GB2012/050002, dated Jul. 12, 2012, 3 pages.
International Search Report mailed Nov. 16, 2010 for International Application No. PCT/GB2010/051066, 8 pages.
Iwasaki, Kazuhide, "Metabolism of Tacrolimus (FK506) and Recent Topics in Clinical Pharmacokinetics," Drug Metab. Pharmacokinet., 22, 5 (2007): 328-335.
Izzo, et al., "Non-psychotropic plant cannabinoids: new therapeutic opportunities from an ancient herb," Trends in Pharmacological Sciences, 30(10):515-527 (2009).
Jacobson, C., "Treating Epilepsy with Pharmaceutical-Grade CBD", Cannabis Science Today, Podcast, 2023, transcript timeline 4 pages; https://agriculturalgenomics.org/podcast/season1/treating-epilepsy-with-pharmaceutical-grade-cbd/.
Jacobson, "Survey of Current Cannabidiol Use in Pediatric Treatment-Resistant Epilepsy," Apr. 22, 2013; https://www.thcint.com/uploads/1/9/3/7/19371199/cannabidiol_use_in_pediatric_epilepsy.pdf, 1 page. Poster.
Jaeger, W. et al., "Inhibition of cyclosporine and tetrahydrocannabinol meabolism by cannabidiol in mouse and human microsomes," Xenobiotica, 26(3):275-284 (1996).
Jiang, R. et al., "Cannabidiol Is a Potent Inhibitor of the Catalytic Activity of Cytochrome P450 2C19," Drug Metab. Pharmacokinet., 28(4):332-338 (2013).
Jones et al. [online], Info & Metrics / Article Information," Cannabidiol Displays Antiepileptic from and Antiseizure Properties in Vitro and in Vivo," J Pharmacol Exp Ther., Feb. 2010, 332(2): 569-577, retrieved on Jun. 25, 2018, URL: http://jpet.aspetjournals.org/content/332/2/569/tab-article-info.
Jones, N. A., Cannabidiol exerts anti-convulsant effects in animal models of temporal lobe and partial seizures, Seizure, 21:344-352, 2012, Published: Apr. 20, 2012. doi:https://doi.org/10.1016/j.seizure.2012.03.001.
Jones, P. G. et al., "Cannabidiol," Acta Cryst., B33:3211-3214 (1977).
Jutras-Aswad, Didier, M.D., M.S. of the Department of Psychiatry for the University of Montreal presents his talk on "CBD in Animal Models and Human Trials of Opiate Abuse," at NYU School of Medicine's Cannabidiol Conference (Oct. 4, 2013). Video published online. http://faces.med.nyu.edu/research-education/cannabidiol-conference, 25 pages.
Kalenderoglou et al., "Cannabidiol Reduces Leukemic Cell Size—But Is It Important?," Front. Pharmacal., Mar. 24, 2017, Sec. Ethnopharmacology, vol. 8-2017, 9 pages; https://doi.org/10.3389/fphar.2017.00144.
Kalepu, S. et al., "Oral lipid-based drug delivery systems—an overview," Acta Pharmaceutica Sinica B., 3(6):361-372 (2013).
Karler, et al., "The cannabinoids as potential antiepileptics," J Clin Pharmacol, 21(8-9 Suppl):437S-447S (1981).
Kassai et al., "Severe Myoclonic epilepsy in Infancy: A Systematic Review and a Meta-Analysis of Individual Patient Data," Epilepsia, 49(2):343-348 (2008).
Katz, Russell ("Rusty"), M.D. former Director of the Division of Neurology Products at the FDA presents his talk on "Dravet and Lennox-Gastaut Syndromes: The Orphan Drug Process," at NYU School of Medicine's Cannabidiol Conference (Oct. 4, 2013). Video published online. http://faces.med.nyu.edu/research-education/cannabidiol-conference, 25 pages.
Kelley, "Medical Cannabis Community Wants to Remain Apart," Kitsap Peninsula Business Journal, Apr. 3, 2013; available at https://www.420magazine.com/community/threads/medical-cannabis-community-wants-to- remain-apart. 186955/, 4 pages.
Kerr, D. N. S. & Pillai, P. M., "Clobazam as adjunctive treatment in refractory epilepsy," British Medical Journal, 286:1246-1247 (1983).
Khan et al., "Key Attributes of TKDL: Laooq-e-Quinnab/Barai Zeequn-Nafs," Khazaain-al-Advia, 1911 (with English translation), 2 pages.
Khan et al., Key Attributes of TKDL: Nushka-e-Qutoor, Muheet-e-Azam, 1887 (with English translation), 2 pages.
Khan et al., "Key Attributes of TKDL: Sufoof-e-Qinnab Barae Waja," Khazaain-al-Adiva, 1911, (with English translation), 5 pages.
Khan et al., "Key Attributes of TKDL: Usaara-e-Qinnab Barai Qoolanj," Khazaain-al-Advia, 1911 (with English translation), 6 pages.
Klonopin Tablets (clonazepam) Klonopin Wafers (clonazepam orally disintegrating tablets) Product Label, revised Apr. 4, 2009, 18 pages.
Kobayashi T., et al., "Renal Carcinogenesis, Hepatic Hemangiomatosis and Embryonic Lethality Caused by a Germ-Line Tsc2 Mutation in Mice," Cancer Research, 1999, 59, pp. 1206-1211.
Koek et al., "Treatment-refractory posttraumatic stress disorder (TRPTSD): a review and framework for the future," Progress in Neuro-Psychopharmacology & Biological Psychiatry, 70:170-218 (2016).
Kopka, M., "Cannabinoids in the treatment of epilepsy—an updated review," Journal of Epileptology, 2019, 27:35-42; 10.21307/jepil-2019-004.
Krasowski, M. D., "Antiepileptic Drugs. Therapeutic Drug Monitoring of the Newer Generation Drugs," Jun. 2013, Clinical Laboratory News, https://www.aacc.org/cln/articles/2013/june/antiepileptic-drugs, 6 pages.
Kwan, P. et al., "Definition of drug resistant epilepsy: consensus proposal by the ad hoc Task Force of the ILAE Commission on Therapeutic Strategies," Epilepsia, 51(6):1069-1077; doi:10.1111/j.1528-1167.2009.02397.x. Epub Nov. 3, 2009. Erratum in: Epilepsia. Sep. 2010; 51(9):1922.
LaBroo et al., "Fentanyl metabolism by human hepatic and intestinal cytochrome P450 3A4: implications for interindividual variability in disposition, efficacy, and drug interactions," Drug Metab Dispos, 25(9): 1072-80 (1997).
LeafScience.com [online], "What are the Highest CBD Strains?" Oct. 15, 2014, retrieved on Feb. 16, 2017, URL www.leafscience.com/2014/10/15/highest-cbd-strains/, 2 pages.
Leahy, J. T. et al., "Clobazam as an adjunctive therapy in treating seizures associated with Lennox-Gastaut syndrome," Neuropsychiatric Disease and Treatment, 7:673-681 (2011).
Leino, A. et al., "Evidence of a clinically significant drug-drug interaction between cannabidiol and tacrolimus: A case report," American Journal of Transplantation, 18 (Suppl. 4): 744-745 (2018).
Leite et al., "New insights from the use of pilocarpine and kainate models," Epilepsy Research, 50:93-103 (2002).

(56) References Cited

OTHER PUBLICATIONS

Leonard, B. E., "Therapeutic Uses of Cannabis," British Medical Association (BMA). Harwood Academic Publishers, UK. 1997, pp. 592.
Lewis, M. M. et al., "Chemical Profiling of Medical Cannabis Extracts," ACS Omega, 2:6091-6103 (2017).
Liu, et al., "Tacrolimus dosage requirements in living donor liver transplant recipients with small-for-size grafts," World Journal Gastroenterol, Aug. 21, 2009, vol. 15(31). pp. 3931-3936.
Lodzki et al., "Cannabidiol—transdermal delivery and anti-inflammatory effect in a murine model," Journal of Controlled Release, 93:377-387 (2003).
Loscher et al., "How theories evolved concerning the mechanism of action of barbiturates," Epilepsia, 53(Suppl. 8):12-25, 2012; doi: 10.1111/epi.12025.
Lowenstein, "Chapter 363: Seizures and Epilepsy," Diseases of the Central Nervous System, 2498-2512 (2008).
Maa et al., "The case for medical marijuana in epilepsy," Epilepsia, 55(6):783-786 (2014); doi: 10.1111/epi.12610.
Malamut, M., "I Drank CBD Coffee for a Week. Here's What I Did to My Anxiety," Nov. 18, 2019, available at https://www.healthline.com/health/mental-health/i-tried-it-cbd-coffee-anxiety, 16 pages.
Manini et al., "Safety and Safety and Pharmacokinetics of Oral Cannabidiol When Administered Concomitantly With Intravenous Fentanyl in Humans," J Addict Med., 9(3): 204-210 (2015);doi: 10.1097/ADM.0000000000000118.
Manno, "Status Epilepticus: Current Treatment Strategies," The Neurohospitalist. Jan. 2011, 1(1):23-31.
Marinol® Product Description, NDA 18-651/S-025 and S-026, Jul. 2006, pp. 3-13.
Marks, W. J. et al., "Management of Seizures and Epilepsy," Am Fam Physician. 1998;57(7):1589-1600.
Masangkay, E. G., "FDA Confirms GW Pharmaceuticals' IND For Epidiolex Trial In Dravet Syndrome," May 9, 2014, 2 pages; FDA Confirms GW Pharmaceuticals' IND For Epidiolex Trial In Dravet Syndrome.
Mead et al., "The Untold Story of the Cannabidiol (CBD) Revolution," US Neurology, 2018; 14(Suppl. 3):2-8. Published Online: Oct. 16, 2018.
Mechoulam et al., "Cannabidiol: an overview of some chemical and pharmacological aspects Part I: chemical aspects," Chemistry and Physics of Lipids 121:35-43 (2002).
Mechoulam et al., "Cannabidiol: An Overview of Some Pharmacological Aspects," J Clin Pharmacol, 2002, 42:11S-19S.
Mechoulam et al., "Hashish-1: The Structure of Cannabidiol," Tetrahedron, 19:2073-2078 (1963).
Mechoulam et al., "The Endocannabinoid System and the Brain," Annu. Rev. Psychol. 2013. 64:21-47.
Mechoulam et al., "Toward drugs derived from cannabis," Naturwissenschaften, 65(4):174-179 (1978).
Mechoulam et al., "Towards a better cannabis drug," British Journal of Pharmacology (2013) 170 1363-1364.
Mechoulam, R., "Conversation with Ralph Mechoulam," Addiction Jun. 2007;102(6):887-93. doi: 10.1111/j.1360-0443.2007.01795.x..
Mechoulam, R., et al., "Cannabidiol-recent advances". Chemistry & Biodiversity (Aug. 2007); 4(8): 1678-1692.
Montenegro et al., "Efficacy of Clobazam as Add-on Therapy for Refractory Epilepsy: Experience at a US Epilepsy Center," Clinical Neuropharmacology, 31(6):333-338 (2008).
Montouris, "Rational approach to treatment options for Lennox-Gastaut syndrome," Epilepsia, 52:10-20 (2011).
Moore, Y. et al., "Cannabidiol reduced frequency of convulsive seizures in drug resistant Dravet Syndrome," Structured Abstracts of Sentinel Articles: Picket, first published Sep. 22, 2017, reported in Arch Dis Child Educ Pract Ed Oct. 2018, vol. 103, No. 5., 2 pages. Abstract.
Morelli et al., "The effects of cannabidiol and its synergism with bortezomib in multiple myeloma cell lines. A role for transient receptor potential Vanilloid type-2," Blood, 110(9):3281-3290 (2014).

Morrison et al., "A Phase 1 Investigation Into the Potential Effects of Cannabidiol on CYP3A4-Mediated Drug-Drug Interactions in Healthy Volunteers," Abstract No. 1.297, Submission ID: 500033, Presentation Date: Dec. 1, 2018, Published Date: Nov. 2018; https://aesnet.org/abstractslisting/a-phase-1- investigation-into-the-potential-effects-of-cannabidiol-on-cyp3a4-mediated-drug-drug-interactions-in-healthy- volunteers, 2 pages.
Morrison et al., "A Phase 1, Open-Label, Pharmacokinetic Trial to Investigate Possible Drug-Drug Interactions Between Clobazam, Stiripentol, or Valproate and Cannabidiol in Healthy Subjects," Clinical Pharmacology in Drug Development, 8(8): 1009-1031 (2019).
Mudigoudar et al., "Emerging Antiepileptic Drugs for Severe Pediatric Epilepsies," Semin Pediatr Neurol, 23:167-179 (2016).
MyVirtualMedicalCentre [online], "Aicardi syndrome," mvmc.com, Feb. 2004, retrieved on Jan. 25, 2019, https://www.myvmc.com/diseases/aicardi-syndrome/, 6 pages.
Nabisi et al., "Cannabinoids synergize with carfilzomib, reducing multiple myeloma cells viability and migration," Oncotarget, 7:77553 (2016).
Nair, A. B. & Jacob, S., "A simple practice guide for dose conversion between animals and human," Basic Clin Pharma, 7(2):27-31 (2016).
Namayandeh et al., "Olive and Sesame Oil Effect on Lipid Profile in Hypercholesterolemie Patients, Which Better?", vol. 4, No. 9, September, pp. 1059-1062. (Year: 2013).
Nathaniel Morris (of Weed Country on Discovery Channel), Selected Media Examples of Pediatric Applications of Cannabidiol, 6 pages, Jun. 23, 2013; available at https://www.youtube.com/watch?v=Mw3wiWkbRg8.
New Drug Application No. 210365 for Epidiolex (cannabidiol) 100 mg/ml oral solution, Jun. 25, 2018, 12 pages.
Ng et al., "Illicit drug use and the risk of new-onset seizures." Am J Epidemiol., 132(1):47-57 (1990).
[No Author Listed] " Convulsive Disorders and their Interference with Driving," Medicos, Retrieved Feb. 10, 2017. Retrieved from the internet URL https://www.medicosporlaseguridadvial.com/en/clinical-subjects/neurologic-diseases/convulsive-disorders-and-their-interference-with-driving, 3 pages.
[No Author Listed] Cannabidiol Therapy for Aicardi Syndrome, Aug. 2014, 4 pages.
[No Author Listed], "Selected Media Examples Of Pediatric Applications Of Cannabidiol (CBD)," Jun. 30, 2013, 4 pages; https://www.420magazine.com/community/threads/selected-media-examples-of-pediatric- appl ications-of-can n abid iol-cbd. 192155/.
[No Author Listed], European Medicines Agency (EMA), "Public summary of opinion on orphan designation—Cannabidiol for the treatment of Dravet syndrome," Nov. 10, 2014, https://www.ema.europa.eu/en/documents/orphandesignation/eu3141339-public-summary-opinion-orphan-designation-cannabidiol-treatment-dravetsyndrome-en.pdf, 4 pages.
[No Author Listed], GW and Otsuka Enter into Gobal Cannabinoid Research Collaboration, News Release, Jul. 9, 2007; https://www.otsuka.co.jp/en/company/newsreleases/2007/20070709_1.html, 4 pages.
[No Author Listed] GW Pharmaceuticals Provides Update on Orphan Program in Childhood Epilepsy for Epidiolex, GW. Pharm. Available online Nov. 14, 2013, Retrieved Feb. 10, 2017, 5 pages.
[No Author Listed], "High Rollers Bet On Cannabidiol (CBD) Medical Marijuana Patients Come Up Short," Mar. 3, 2013, 9 pages; https://www.420magazine.com/community/threads/high-rollers-bet-on- cannabidiol-cbd-% E2%80%94-medical-marijuana-patients-come-up-short. 185325/.
[No Author Listed] "ILAE Proposal for Revised Terminology for Organization of Seizures and Epilepsies," 2010, 2 pages.
[No Author Listed], License Agreement between GW Pharma and GW Pharmaceuticals, PLC and Otsuka, Feb. 2007;https://www.sec.gov/Archives/edgar/data/1351288/000104746913003351/a2213875zex-10_16.htm, 63 pages.
[No Author Listed], "Medical Cannabis Community Wants To Remain Apart," Medical Marijuana News, Apr. 3, 2013, 3 pages; Kitsap Peninsula Business Journal, available at: https://www.420magazine.com/community/threads/medical-cannabis-community-wants-to-remain- apart.186955/.

(56) References Cited

OTHER PUBLICATIONS

[No Author Listed], "Medical Marijuana For N.J. Children? It's All In Gov. Christie's Hands," CBS News New York, Jun. 27, 2013, 3 pages; https://www.cbsnews.com/newyork/news/medical-marijuana-for-n-j- children-its-all-in-gov-christies-hands/.

[No Author Listed], "Missouri House passes cannabis extract legislation," Kansas City Star, 2014, https://kansascity.com/news/politics-government/article346747.html, 2 pages.

[No Author Listed] "Orphan Drug Designation Granted for Epidiolex in Drave syndrome by the FDA- Seven Expanded Access INDs granted by FDA to US physicians to treat with Epidiolex 125 children suffering from intractable epilepsy dyndromes," GW Pharma Press Release, dated Nov. 14, 2013, 3 pages.

[No Author Listed], "Photo Release—Kannaway Back office Goes Live CBD-Rich Hemp Oil Products Offered for Sale," May 7, 2014, Globe Newswire, https://www.globenewswire.com/en/news-release/2014/05/07/634020/30927/en/Photo-Release-Kannaway-Back-Office-Goes-Live-CBD-Rich-Hemp-Oil- Products-Offered-for-Sale.html, 6 pages.

[No Author Listed] Salutaris Drops Buy Salutaris Drops—Salutaris Drops. Oct. 12, 2014. Last accessed on Jan. 20, 2017 from http://web.archive.org/web/ 20141012130255/ http://salutaris drops.com/buy-salutaris-drops/, 2 pages.

[No Author Listed], The Reuters Staff, BRIEF-GW Pharma receives FDA fast-track designation for Dravet syndrome treatment, Jun. 6, 2014, 1 page; https://www.reuters.com/article/gwpharmaceuticals-brief/brief-gw-pharma-receives-fda-fast-track-designation-for-dravet-syndrome-treatment-idUSFWNOOL01D20140606.

[No Author Listed] "What are the Highest CBD Strains?" Oct. 15, 2014, retrieved on Feb. 16, 2017, URL www.leafscience.com/2014/10/15/highest-cbd-strains/, 2 pages.

Non-Final Action for U.S. Appl. No. 13/380,305 mailed Aug. 25, 2014, 6 pages.

Notice of Opposition to a European Patent Application No. EP15784111.5, Patent No. EP3206716, dated May 10, 2021, 25 pages.

Notice of Opposition to European Patent Application No. EP18737374.1, Patent No. EP3641819, dated Jul. 12, 2024, 23 pages.

Notice of Opposition to European Patent Application No. EP19702670.1, Patent No. EP3743053, dated Aug. 27, 2024, 22 pages.

Oguni, H. et al., "Severe myoclonic epilepsy in infants—a review based on the Tokyo women's Medical University series of 84 cases," Brain Dev., 23:736-748 (2010).

Oguni, H. et al., "Long-Term Prognosis of Lennox-Gastaut Syndrome," Epilepsia, 37(Suppl 3):44-47 (1996).

Olyaei, A. J. et al., "Interaction Between Tacrolimus and Nefazodone in a Stable Renal Transplant Recipient," Pharmacotherapy, 18(6):1356-1359 (1998).

Onfi'm (clobazam) tablets Prescribing Information, NDA 202067
Onfi (clobazam) Tablets for oral use FDA Approved Labeling Text, dated Oct. 21, 2011, 28 pages.

Opponent Response dated to Sep. 9, Preliminary 2016, 25 Opinion pages of the Opposition Division in European Patent No. EP2448637, dated Sep. 9, 2016.

Ostendorf, A. P. & NG, Y-T., "Treatment-resistant Lennox-Gastaut syndrome: therapeutic trends, challenges and future directions," Neuropsychhiatric Disease and Treatment, 13:1131-1140 (2017).

Palmer, A. C. et al., "Combination Cancer Therapy Can Confer Benefit via Patient-to-Patient Variability without Drug Additivity or Synergy," Cell, 171:1678-1691 (2017).

Panikasiwill, D. et al., "An endogenous cannabinoid (2-AG) is neuroprotective after brain injury," Nature 413:527-531 (2001).

Patent Owners' Preliminary Response for IPR2017-00503 dated Apr. 11, 2017, 1 page.

Patsalos et al., "Clinical implications of trials investigating drug-drug interactions between cannabidiol and enzyme inducers or inhibitors or common antiseizure drugs," Epilepsia, 61:1854-1868 (2020).

PCT International Preliminary Report on Patentability in International Appln. No. PCT/US2017/050868, dated Jun. 18, 2019, 8 pages, 11 pages.

PCT International Search Report and Written Opinion in International Appln. No. PCT/US2017/050868, dated Jun. 21, 2018, 11 pages.

Pelliccia, A. et al., "Treatment with CBD in oily solution of drug-resistant paediatric epilepsies," 2005 Congress on Cannabis and the Cannabinoids, Leiden, The Netherlands: International Association for Cannabis as Medicine, p. 14., Abstract, 2 pages.

Pellicia, et al., International Association for Cannabis as Medicine, IACM 3rd Conference on Cannabinoids in Medicine, Sep. 9-10, 2005, 2005 Conference on Cannabinoids in Medicine, 72 pages.

Pertwee, "Cannabidiol as a potential medicine," In: Mechoulam, R. (eds) Cannabinoids as Therapeutics. Milestones in Drug Therapy MDT (2005), pp. 47-65, Birkhauser Basel, https://doi.org/10.1007/3-7643-7358- X_3.

Pertwee, R. G., "The Pharmacology and Therapeutic Potential of Cannabidiol," Cannabinoids, Chapter 3, DiMarzo, V. (Ed.), pp. 32-83 (2004).

Perucca, "Cannabinoids in the Treatment of Epilepsy: Hard Evidence at Last?" Journal of Epilepsy Research, 7(2):61-76 (2017).

Petitioner's Reply to Patent Owner's Response in Inter Partes Review No. IPR2017-00503, filed Jan. 19, 2018, 1 page.

Porter et al., "Randomized, multicenter, dose-ranging trial of retigabine for partial-onset seizures," Neurology, 68(15):1197-1204 (2007).

Porter et al., "Report of a parent survey of cannabidiol-enriched cannabis use in pediatric treatment-resistant epilepsy," Epilepsy Behav., 29(3):574-577 (2013).

Pot or not? Why parents of kids with epilepsy want access to marijuana treatment, CTVNews.ca Staff, Published Thursday, Jul. 18, 2013; Last Updated Thursday, Jul. 18, 2013, 2 pages; treatment-1.1372695?cache=.https://www.ctvnews.ca/health/health-headlines/pot-or-not-why-parents-of-kids-with-epilepsy-want-access-tomarijuana-.

Potter, C., "Cannabis Extract Brings Hope for Children with Epilepsy," Dec. 3, 2013, 3 pages.

Pouton, "Lipid formulations for oral administration of drugs: non-emulsifying, self-emulsifying and 'self-micro emulsifying' drug delivery systems," Eur J Pharm Sci, 11(Suppl. 2):S93-S98 (2000).

Press, et al., "Parental reporting of response to oral cannabis extracts for treatment of refractory epilepsy," Epilepsy Behav. Apr. 2015; 45:49-52. doi: 10.1016/j.yebeh.2015.02.043. Epub Apr. 3, 2015.

Purcarin, G. & NG, Y-T., "Experience in the use of clobazam in the treatment of Lennox-Gastaut syndrome," Ther Adv Neurol Disord 2014, vol. 7(3):169-176.

Raab et al., "Multiple myeloma," Lancet, 374(9686):314-339 (2009).

Racha, K.J., et al., "Substrate Dependent Inhibition Profiles of Fourteen Drugs on CYP3A4 Activity Measured by A High Throughput LCMS JMS Method with Four Probe Drugs, Midazolam, Testosterone, Nifedipine and Terfenadine," Drug Metabolism and Pharmacokinetics, Dec. 27, 2003, vol. 18 (2), pp. 128-138.

Ragona, F. et al., "Dravet syndrome: early clinical manifestations and cognitive outcome in 37 Italian patients," Brain Dev., 32:71-77 (2010).

Reply to Communication from the examining Division in European Patent Application No. 10734541.5 dated Feb. 15, 2013, 54 pages.

Reply to EPO Communication in European Patent No. EP2448637, dated Nov. 2, 2016, 45 pages.

Request for Continued Examination with Amendment and Information Disclosure Statement in U.S. Appl. No. 13/380,305, filed Mar. 2, 2015, 3 pages.

Resstel et al., "5-HTIA receptors are involved in the cannabidiol-induced attenuation of behavioural and cardiovascular responses to acute restraint stress in rats," Br J Pharmacol. Jan. 2009; 156(1): 181-8.

Rison, R. A., "How to write a neurology case report," Journal of Medical Case Reports, 10:91 (2016); doi:10.1186/s13256-016-0867-x, 5 pages.

Rohrback, Brian G., Ph.D, MBA President of Infometrix, Inc. presents his talk on "Assays of Cannabinoids," at NYU School of Medicine's Cannabidiol Conference (Oct. 4, 2013). Video published online. http://faces.med.nyu.edu/research-education/cannabidiol-conference, 29 pages.

(56) References Cited

OTHER PUBLICATIONS

Romano et al., "Inhibition of colon carcinogenesis by a standardized Cannabis sativaextract with high content of cannabidiol," Phytomedicine, 21:631-639 (2014).
Rosenberg et al., "Cannabinoids and Epilepsy," Neurotherapeutics, Oct. 2015, 12(4): 747-768.
Rosenkrantz et al., "Inhalation, Parenteral and Oral LD50 Values of 119-Tetrahydrocannabinol in FischerRats," Toxicology and Applied Pharmacology, 28:18-27 (1974).
Rosenkrantz et al., "Oral and Parenteral Formulations of Marijuana Constituents," J Pharm Sci, 61(7):1106-1112 (1972).
Rosenkrantz et al., "Toxicity of Short-Term Administration of Cannabinoids to Rhesus Monkeys," Toxicology and Applied Pharmacology, 58:118-131 (1981).
Rowe, R. C. et al., "Handbook of Pharmaceutical Excipients," Pharmaceutical Press and American Pharmacists Association 2009, pp. 17-19; https://www.academia.edu/16731682/Handbook_of_Pharmaceutical_Excipients_6th_Edition.
Saad, D. & Joshi, C., "Pure Cannabidiol in the Treatment of Malignant Migrating Partial Seizures in Infancy: A Case Report," Pediatric Neurology, 52:544-547 (2015).
SalutarisDrops.com [ online], "Cannabidiol for Aicardi Syndrome," Salutaris, available on or before Oct. 2014, retrieved on Feb. 10, 2017, URL http://web.archive.org/web/20141012220050/ http://salutarisdrops.corn/cannabidiol-aicardi-syndrome/, 3 pages.
Samanta, D., "Cannabidiol: A Review of Clinical Efficacy and Safety in Epilepsy," Pediatric Neurology, 96:24-29 (2019).
Samara et al., "Pharmacokinetics of Cannabidiol in Dogs," Drug Metabolism and Disposition, 16(3):469-472 (1988).
Sands, T. T. et al., "Long-Term Safety, Tolerability, and Efficacy of Cannabidiol in Children with Refractory Epilepsy: Results from an Expanded Access Program in the US," CNS Drugs, 33:47-60 (2019); https://doi.org/10.1007/s40263-018-0589-2.
Sasidharan, S. et al., "Extraction, Isolation and Characterization of Bioactive Compounds from Plants' Extracts," Afr J Tradit Complement Altern Med., 8(1):1-10 (2018).
Schafroth et al., "119-cis-Tetrahydrocannabinol: Natural Occurrence, Chirality, and Pharmacology," Journal of Natural Products, 84:2502-2510 (2021).
Schafroth, M. A. et al., "Sterodivergent Total Synthesis of Δ9-Tetrahydrocannabinols," Angew. Chem. Int. Ed., 53:13898-13901 (2014).
Scheffer, I. E., "Diagnosis and long-term course of Dravet syndrome," Eur J of Paediatric Neurology 16 (2012) S5-S8.
Schwieterman, M. L. et al., "Strawberry Flavor: Diverse Chemical Compositions, a Seasonal Influence, and Effects on Sensory Perception," PLoS ONE, 9(2): e88446 (2014); doi:10.1371/journal.pone.0088446, 12 pages.
Screenshot confirming date of Epidiolex (Cannabidiol) in Treatment Resistant Epilepsy, Apr. 2015; https://epilepsyontario.org/wp-content/uploads/2015/Epidiolex-Cannabidiol-in-Treatment-Resistant-Epilepsy AAN-POSTER 08Apr2015.pdf, 1 page.
Serra I., et al., "Cannabidiol modulates phosphorylated rpS6 signalling in a zebrafish model of Tuberous Sclerosis Complex," Behavioural Brain Research, 2019, 363, pp. 135-144.
Shih, J. J. et al., "Epilepsy treatment in adults and adolescents: Expert opinion, 2016," Epilepsy & Behavior, 69:186-222 (2017).
Silva et al., "Clobazam as Add-on Therapy in Children with Epileptic Encephalopathy," Can. J. Neurol. Sci., 33:209-213 (2006).
Silva et al., "Position Statement on the Use of Medical Cannabis for the Treatment of Epilepsy in Canada," Can J. Neurol. Sci., 33:783-786 (2006).
Silvestro, S. et al., "Use of Cannabidiol in the Treatment of Epilepsy: Efficacy and Security in Clinical Trials," Molecules, 24:1459 (2019), 25 pages; doi:10.3390/molecules24081459.
Sirven et al., Finding the Best Dosage of Medication, Epilepsy Foundation (Mar. 19, 2014); https://www.epilepsy.com/treatmenVmedicines/finding-best-dosage, 11 pages.
Sluss, R. J., "Comparison of Artificial Flavors in Commercial Products and Actual Natural Flavor via Gas Chromatography Mass Spectroscopy Data." (2009). Electronic Theses and Dissertations. Paper, 1804; https://dc.etsu.edu/etd/1804, 72 pages.
Smith, R. M. & Kempfert, K. D., "LIL3,4-C/S-Tetrahydrocannabinol in Cannabis Sativa," Phytochemistry, 16:1088-1089 (1977).
Smith, R. M., "Identification of Butyl Cannabinoids in Marijuana," Journal of Forensic Sciences, 42:610-618 (1997).
Specchio, L. M. & Beghi, E., "Should Antiepileptic Drugs Be Withdrawn in Seizure-Free Patients" CNS Drugs, 18(4):201-212 (2004).
Stafstrom et al., "Models of Pediatric Epilepsies: Strategies and Opportunities," Epilepsia, 47(8):1407-1414 (2006).
Stewart, K., "Families migrating to Colorado for a medical marijuana miracle," Nov. 11, 2013, 8 pages; https://archive.sltrib.com/article.phpid=57052556&itype=CMSID.
Stinchcomb, A. L. et al., "Human skin permeation of Δ8-tetrahydrocannabinol, cannabidiol and cannabinol," JPP 2004, 56: 291-297.
Strickley, R. G., (Feb. 2004), "Solubilizing Excipients in Oral and Injectable Formulations," Pharmaceutical Research, vol. 21, No. 2, pp. 201-230.
Subduction Coffee + Hemp, Product Page, 2023, 5 pages; https://subductioncoffee.com/?afmc=2j&utm_campaing=2j&utm_source=leaddyno&utm_medium=affiliate.
Sun et al., "Comparative study of organic solvent and water-soluble lipophilic extractives from wheat straw 1: yield and chemical composition," J Wood Sci, 49:47-52 (2003).
Swann et al., "The effects of seizures on the connectivity and circuitry of the developing brain," Ment Retard Dev Disabil Res Rev., 10(2):96-100 (2004).
Tang J et al., "Application of Machine-learning Models to Predict Tacrolimus Stable Dose in Renal Transplant Recipients," Scientific Reports, Feb. 8, 2017:7:42192, 10 pages.
Tanya Lewis, Mystery Mechanisms, The Scientist Magazine, Jul. 29, 2016, 2 pages; http://www.the- scientist.com/.
Thiel, E. A., "Managing Epilepsy in Tuberous Sclerosis Complex," J Child Neurol 2004; 19:680-686.
Third Party Observations for Application No. AU2012314128, mailed Mar. 19, 2015, 51 pages.
Thomas et al., "Characterization of the Lipophilicity of Natural and Synthetic Analogs of Δ9- Tetrahydrocannabinol and Its Relationship to Pharmacological Potency," The Journal of Pharmacology and Experimental Therapeutics, 255(2):624-630 (1990).
Thomas et al., "Evidence that the plant cannabinoid Delta9-tetrahydrocannabivarin is a cannabinoid CBI and CB2 receptor antagonist," Br J Pharmacol., 146(7):917-926 (2005).
Thompson et al., "Comparison of acute oral toxicity of cannabinoids in rats, dogs and monkeys," Toxicology and Applied Pharmacology, vol. 25, Issue 3, pp. 363-372 (1973).
Thompson et al., "Oral and Intravenous Toxicity of 119-Tetrahydrocannabinol in Rheus Monkeys," Toxicology and Applied Pharmacology, 27:648-665 (1974).
Tose, L. V. et al., "Isomeric separation of cannabinoids by UPLC combined with ionic mobility mass spectrometry (TWIM-MS)Part I," International Journal of Spectrometry, 418:112-121 (2017).
Transcript of Dr. H. Steven White's deposition, dated Dec. 29, 2017, 69 pages.
Trost, B. M. & Dogra, K., "Synthesis of (−)-Δ9-trans-Tetrahydrocannabinol: Stereocontrol via Mo-Catalyzed Asymmetric Allylic Alkylation Reaction," Organic Letters, 9(5):861-863 (2007).
Turkanis et al., "Excitatory and Depressant Effects of Delta-9-Tetrahydrocannabidinol and Cannabidiol on Cortical Evoked Responses in the Conscious Rat," Psychopharmacology, 75:294-298 (1981).
Uliss et al., "The conversion of 3,4-C/S- to 3,4- TRANS-cannabinoids," Tetrahedron, 34:1885-1888 (1978).
University of Utah doctors: Say 'yes' to cannabis oil for kids, By Kirsten Stewart The Salt Lake Tribune, Nov. 13, 2013, 4 pages.
U.S. Department of Health and Human Services, Food and Drug Administration Center for Drug Evaluation and Research (CDER), "Guidance for Industry Estimating the Maximum Safe Starting Dose in Initial Clinical Trials for Therapeutics in Adult Healthy Volunteers," Jul. 2005, 30 pages.
U.S. Appl. No. 15/640,033, filed Jun. 30, 2017, by Wilkhu et al.

(56) References Cited

OTHER PUBLICATIONS

U.S. Appl. No. 16/768,241, filed May 29, 2020, by Guy et al.
U.S. Appl. No. 16/935,005, filed Jul. 21, 2020, by Guy et al.
U.S. Appl. No. 16/959,354, filed Jun. 30, 2020, by Wilkhu et al.
U.S. Appl. No. 17/296,066, filed May 21, 2021, by Guy et al.
U.S. Appl. No. 17/296,076, filed May 21, 2021, by Guy et al.
U.S. Appl. No. 17/406,401, filed Aug. 19, 2021, by Wilku et al.
U.S. Appl. No. 17/424,682, filed Jul. 21, 2021, by Guy et al.
U.S. Appl. No. 17/435,892, filed Sep. 2, 2021, by Guy et al.
U.S. Appl. No. 17/585,415, filed Jan. 26, 2022, by Whalley et al.
U.S. Appl. No. 17/627,946, filed Jan. 18, 2022, by Silcock et al.
U.S. Appl. No. 17/689,607, filed Mar. 8, 2022, by Guy et al.
U.S. Appl. No. 17/770,435, filed Apr. 20, 2022, by Guy et al.
U.S. Appl. No. 17/771,184, filed Apr. 22, 2022, by Guy et al.
U.S. Appl. No. 17/771,190, filed Apr. 22, 2022, by Guy et al.
U.S. Appl. No. 17/771,195, filed Apr. 22, 2022, by Guy et al.
U.S. Appl. No. 17/777,677, filed May 18, 2022, by Guy et al.
U.S. Appl. No. 17/777,681, filed May 18, 2022, by Guy et al.
U.S. Appl. No. 17/777,734, filed May 18, 2022, by Guy et al.
U.S. Appl. No. 17/786,949, filed Jun. 17, 2022, by Silcock et al.
U.S. Appl. No. 17/853,367, filed Jun. 29, 2022, by Guy et al.
U.S. Appl. No. 18/002,437, filed Dec. 19, 2022, by Li et al.
U.S. Appl. No. 18/005,843, filed Jan. 17, 2023, by Checketts et al.
U.S. Appl. No. 18/005,848, filed Jan. 17, 2023, by Checketts et al.
U.S. Appl. No. 18/005,852, filed Jan. 18, 2023, by Checketts et al.
U.S. Appl. No. 18/005,853, filed Jan. 18, 2023, by Checketts et al.
U.S. Appl. No. 18/005,868, filed Jan. 18, 2023, by Checketts et al.
U.S. Appl. No. 18/006,121, filed Jan. 19, 2023, by Checketts et al.
U.S. Appl. No. 18/006,127, filed Jan. 19, 2023, by Checketts et al.
U.S. Appl. No. 18/006,129, filed Jan. 19, 2023, by Checketts et al.
U.S. Appl. No. 18/006,131, filed Jan. 19, 2023, by Checketts et al.
U.S. Appl. No. 18/043,810, filed Mar. 2, 2023, by Loft et al.
U.S. Appl. No. 18/044,941, filed Mar. 10, 2023, by Craig et al.
U.S. Appl. No. 18/161,603, filed Jan. 30, 2023, filed Whalley et al.
U.S. Appl. No. 18/170,235, filed Feb. 16, 2023, by Guy et al.
U.S. Appl. No. 18/186,792, filed Mar. 20, 2023, by Guy et al.
U.S. Appl. No. 18/256,307, filed Jun. 7, 2023, by Checketts et al.
U.S. Appl. No. 18/257,373, filed Jun. 14, 2023, by Silcock et al.
U.S. Appl. No. 18/257,479, filed Jun. 14, 2023, by Tse et al.
U.S. Appl. No. 18/257,537, filed Jun. 14, 2023, by Silcock et al.
U.S. Appl. No. 18/258,485, filed Jun. 20, 2023, by Craig et al.
U.S. Appl. No. 18/292,844, filed Jan. 26, 2024, by Knappertz et al.
U.S. Appl. No. 18/311,221, filed May 2, 2023, by Guy et al.
U.S. Appl. No. 18/446,405, filed Aug. 8, 2023, by Guy et al.
U.S. Appl. No. 18/477,467, filed Sep. 28, 2023, by Wilkhu et al.
U.S. Appl. No. 18/526,795, filed Dec. 1, 2023, by Guy et al.
U.S. Appl. No. 18/546,254, filed Aug. 11, 2023, by Tse et al.
U.S. Appl. No. 18/548,003, filed Aug. 25, 2023, by Knappertz et al.
U.S. Appl. No. 18/560,316, filed Nov. 10, 2023, by Silcock et al.
U.S. Appl. No. 18/560,337, filed Nov. 10, 2023, by Silcock et al.
U.S. Appl. No. 18/560,341, filed Nov. 10, 2023, by Silcock et al.
U.S. Appl. No. 18/560,346, filed Nov. 10, 2023, by Silcock et al.
U.S. Appl. No. 18/597,717, filed Mar. 6, 2024, by Whitehouse et al.
U.S. Appl. No. 18/762,588, filed Jul. 2, 2024, by Guy et al.
U.S. Appl. No. 18/859,454, filed Oct. 23, 2024, by Chen et al.
U.S. Appl. No. 18/862,705, filed Nov. 4, 2024, by Straker et al.
U.S. Appl. No. 18/874,175, filed Dec. 12, 2024, by Straker et al.
U.S. Appl. No. 18/912,442, filed Oct. 10, 2024, by Guy et al.
U.S. Appl. No. 18/921,741, filed Oct. 21, 2024, by Guy et al.
U.S. Appl. No. 19/024,770, filed Jan. 16, 2025, by Guy et al.
U.S. Appl. No. 19/102,763, filed Feb. 10, 2025, by Whalley et al.
USPTO Notice of Allowance in U.S. Appl. No. 13/380,305, dated Dec. 10, 2014, 5 pages.
USPTO Notice of Allowance in U.S. Appl. No. 13/380,305, dated Mar. 19, 2015, 7 pages.
Van Bakel et al., "The draft genome and transcriptome of Cannabis sativa," Genome Biology 2011, 12:R102, 18 pages; http://genomebiology.com/2011/12/10/R102 (Oct. 24, 2011).
Van Straten et al., "Update on the Management of Lennox-Gastaut Syndrome," Pediatric Neurology, 47:153-161 (2012).
Velasco et al., "Anticancer mechanisms of cannabinoids," Curr Oncol, 23(2):S23-S32 (2016).
Velisek, "Chapter 11: Models of Chemically-Induced Acute Seizures," Models of Seizures and Epilepsy, pp. 127-152 (2006).
Vezyroglou, K. & Cross, J. H., "Targeted Treatment in Childhood Epilepsy Syndromes," Curr Treat Options Neurol, 18:29 (2016), Published online May 7, 2016. doi: 10.1007/s11940-016-0407-4, 12 pages.
Vrielynck, P., "Current and emerging treatments for absence seizures in young patients," Neuropsychiatric Disease and Treatment, 9:963-975 (2013).
Wallace et al., "Assessment of the role of CB 1 receptors in cannabinoid anticonvulsant effects," Eur J Pharmacol. Sep. 28, 2001;428(1):51-7.
Wallace et al., "Pharmacotherapy for Dravet Syndrome," Pediatr. Drugs, 18:197-208 (2016).
Warzak et al., "Caffeine Consumption in Young Children," The Journal of Pediatrics, vol. 158, Issue 3, pp. 508-509, Mar. 1, 2011.
Weed Country, Episode 5, 2013; https://www.youtube.com/watch?v=OisjCcMtxBk; https://www.youtube.com/watch?v=GitMYGvwC4E&t=212s, 25 pages.
Weed Country, Episode 6, 2013; https://www.youtube.com/watch?v=Uyzuy1fNQfQ, 18 pages.
Weed Wars, Video I, Dec. 10, 2011, Weed Wars: The Story of Jayden-Andrew DeAngelo; https://www.youtube.com/watch?v=2WizdR5uHj0, no page Nos. available.
Weed Wars, Video II, May 25, 2013, 3 pages; available at https://www.youtube.com/watch?v=XBX_DB9sw5U.
Weedwars, CNN Special, Decriminialise It, Dr. Sanjay Gupta, 2013; https://www.youtube.com/watch?v=Z3IMfl1_K6U, 8 pages.
Weimer-Kruel, A. et al., "Cannabidiol Interacts Significantly with Everolimus—Report of a Patient with Tuberous Sclerosis Complex," Neuropediatrics, 50(6), 2019, 4 pages; doi:https://doi.org/10.1055/s-0039- 1695786.
Whalley, Benjamin J. Ph.D. of the University of Reading presents his talk on "Cannabis and Epilepsy: Cannabidiol (CBD) and Cannabidavarin (CBDV) in Preclinical Models of Seizure and Epilepsy," at NYU School of Medicine's Cannabidiol Conference (Oct. 4, 2013). Video published online. http://faces.med.nyu.edu/research-education/cannabidiol-conference, 30 pages.
Wheless, J. W. et al., "Pharmacokinetics and Tolerability of Multiple Doses of Pharmaceutical-Grade Synthetic Cannabidiol in Pediatric Patients with Treatment-Resistant Epilepsy," CNS Drugs, 33(6):593-604 (2019); doi: 10.1007/s40263-019-00624-4.
Whittle et al., (2001). Prospects for New Cannabis-Based Prescription Medicines. Journal of Cannabis Therapeutics. 1(3-4); doi:10.1300/J175v01, 1(3-4), 23 pages.
Wikipedia.org [online], "Cannabinoid," Wikipedia, Apr. 2003, retrieved on Mar. 1, 2017, URL https://en.wikipedia.org/wiki/Cannabinoid, 15 pages.
Wilkey, R., "'Weed Wars': Five-Year-Old Takes Medical Marijuana On Reality Show (Video)", Dec. 10, 2011, 7 pages; https://www.huffpost.com/entry/weed-wars-five-year-old-smokes-marijuana_n_1140351.
Williams, "The Key to Healing Broken Bones May be Found in This Illegal Drug," Jul. 25, 2015; https://www.fool.com/investing/high-growth/2015/07/25/the-key-to-healing-broken-bones-may-be-found-in-th.aspx#:~:text=As%20published%20in%20the%20Journal,rats%20in%20just%20eight%20 weeks, 5 pages.
Willis, L., "Final Report on the Safety Assessment of Sesame Oil," Journal of the American College of Toxicology, 12(3):261-277 (1993).
Wirrell, E. C., "Treatment of Dravet Syndrome," Can J Neurol Sci., 43: S13-S18 (2016).
Wright et al., Cannabidiol (CBD) in Dravet Syndrome: A Randomised, Dose-Ranging Pharmacokinetics and Safety Trial (GWPCARE1), Epilepsia, 58(Suppl. 5):S5-S199 (2017), p0240 Abstract, 1 page.
Yamaori, S. et al., "Potent inhibition of human cytochrome P450 3A isoforms by cannabidiol: Role of phenolic hydroxyl groups in the resorcinol moiety," Life Sciences, 88:730-736 (2011).
Young, S., "Marijuana stops child's severe seizures," CNN Health online, Aug. 7, 2013, 4 pages; https:/ /www. en n. com/20 13/08/ 07 /health/ch arl otte-ch i ld-med ical-marij u ana/index. htm

(56) References Cited

OTHER PUBLICATIONS

1#: -:text= The%20first%20time%20Paige%20Figi, seizures%20stopped%20for%20seven% 20days. &text=The%20marijuana%20strain%20Charlotte%20and, has%20been%20named%20after%20her.

Zhang, T. et al., "Pre-seizure state identified by diffuse optical tomography," Scientific Reports, 4:3798 (2014); https://doi.org/10.1038/srep03798, 10 pages.

Zhornitsky, S. and S. Potvin (2012) Cannabidiol in Humans—The Quest for Therapeutic Targets. Pharmaceuticals, 5:529-552; doi: 10.3390/ph5050529.

Zuardi A., et al., "Inverted U-Shaped Dose-Response Curve of the Anxiolytic Effect of Cannabidiol during Public Speaking in Real Life," Frontiers in Pharmacology 2017, 8, Article 259, pp. 1-9.

Zuardi et al., "Antipsychotic Effect of Cannabidiol," J Clin Psychiatry, 56(10):485-486 (1995).

Zuardi et al., "Cannabidiol for the treatment of psychosis in Parkinson's disease," Journal of Psychopharmacology, 23(8):979-983 (2009).

Zuardi et al., "Cannabidiol: from an inactive cannabinoid to a drug with wide spectrum of action," Rev Bras Psiquiatr, 30(3):271-280 (2008).

\* cited by examiner

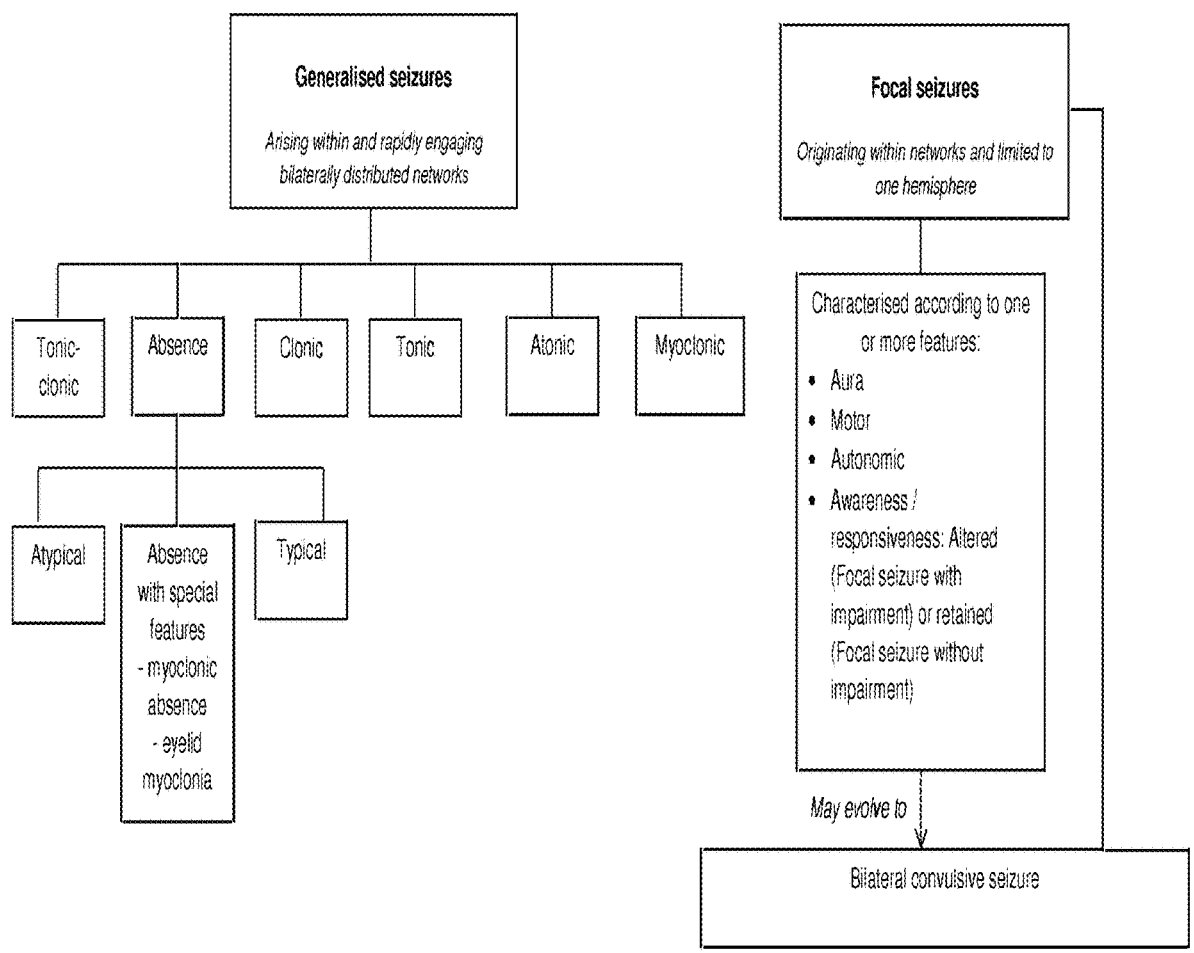
Figure 1. ILAE Proposal for Revised Terminology for Organisation of Seizures and Epilepsies 2010

USE OF CANNABINOIDS IN THE TREATMENT OF EPILEPSY

CROSS-REFERENCE TO RELATED APPLICATIONS

This application is a continuation of U.S. patent application Ser. No. 18/186,792, filed Mar. 20, 2023, which is a continuation of U.S. patent application Ser. No. 17/819,046, filed Aug. 11, 2022, now U.S. Pat. No. 11,633,369, which is a continuation of U.S. patent application Ser. No. 17/477,172, filed Sep. 16, 2021, now U.S. Pat. No. 11,446,258, issued Sep. 20, 2022, which is a continuation of U.S. patent application Ser. No. 17/242,075, filed Apr. 27, 2021, now U.S. Pat. No. 11,154,517, issued Oct. 26, 2021, which is a continuation of Ser. No. 17/198,965, filed Mar. 11, 2021, now U.S. Pat. No. 11,096,905, issued Aug. 24, 2021, which is a continuation of U.S. patent application Ser. No. 16/911,914, filed Jun. 25, 2020, now U.S. Pat. No. 10,966,939, issued Apr. 6, 2021, which is a continuation of U.S. Patent application Ser. No. 16/198,141, filed Nov. 21, 2018, now U.S. Pat. No. 10,849,860, issued Dec. 1, 2020, which is a continuation of U.S. patent application Ser. No. 15/449,535, filed Mar. 3, 2017, now U.S. Pat. No. 10,137,095, issued Nov. 27, 2018, which is a continuation of Ser. No. 14/881,969, filed Oct. 13, 2015, now U.S. Pat. No. 10,111,840, issued Oct. 30, 2018, which claims priority to GB 1418171.3, filed Oct. 14, 2014. Each of these applications is incorporated herein by reference in its entirety.

FIELD OF THE INVENTION

The present invention relates to the use of cannabidiol (CBD) in the treatment of atonic seizures. In one embodiment the patients suffering from atonic seizures are children and young adults CBD appears particularly effective in reducing atonic seizures in patients suffering with etiologies that include: Lennox-Gastaut Syndrome; Tuberous Sclerosis Complex; Dravet Syndrome; Doose Syndrome; Aicardi syndrome; CDKL5 and Dup15q in comparison to other seizure types.

In these patients treatment with CBD reduced the occurrence of atonic seizures by greater than 50% in a large proportion, namely 63%, of patients. This was surprising given that the proportion of patients benefitting from a greater than 50% reduction in total seizures was significantly less, (46%), in all subjects treated.

Preferably the CBD used is in the form of a highly purified extract of *cannabis* such that the CBD is present at greater than 98% of the total extract (w/w) and the other components of the extract are characterised, in particular the cannabinoid tetrahydrocannabinol (THC) has been substantially removed, to a level of not more than 0.15% (w/w) and the propyl analogue of CBD, cannabidivarin, (CBDV) is present in amounts of up to 1%. Alternatively, the CBD may be a synthetically produced CBD.

In use the CBD may be given concomitantly with one or more other anti-epileptic drugs (AED). Alternatively the CBD may be formulated for administration separately, sequentially or simultaneously with one or more AED or the combination may be provided in a single dosage form. Where the CBD is formulated for administration separately, sequentially or simultaneously it may be provided as a kit or together with instructions to administer the one or more components in the manner indicated. It may also be used as the sole medication, i.e. as a monotherapy.

BACKGROUND TO THE INVENTION

Epilepsy occurs in approximately 1% of the population worldwide, (Thurman et al., 2011) of which 70% are able to adequately control their symptoms with the available existing anti-epileptic drugs (AED). However, 30% of this patient group, (Eadie et al., 2012), are unable to obtain seizure freedom from the AED that are available and as such are termed as suffering from intractable or "treatment-resistant epilepsy" (TRE).

Intractable or treatment-resistant epilepsy was defined in 2009 by the International League Against Epilepsy (ILAE) as *"failure of adequate trails of two tolerated and appropriately chosen and used AED schedules (whether as monotherapies or in combination) to achieve sustained seizure freedom"* (Kwan et al., 2009).

Individuals who develop epilepsy during the first few years of life are often difficult to treat and as such are often termed treatment-resistant. Children who undergo frequent seizures in childhood are often left with neurological damage which can cause cognitive, behavioral and motor delays.

Childhood epilepsy is a relatively common neurological disorder in children and young adults with a prevalence of approximately 700 per 100,000. This is twice the number of epileptic adults per population.

When a child or young adult presents with a seizure, investigations are normally undertaken in order to investigate the cause. Childhood epilepsy can be caused by many different syndromes and genetic mutations and as such diagnosis for these children may take some time.

The main symptom of epilepsy is repeated seizures. In order to determine the type of epilepsy or the epileptic syndrome that a patient is suffering from an investigation into the type of seizures that the patient is experiencing is undertaken. Clinical observations and electroencephalography (EEG) tests are conducted and the type(s) of seizures are classified according to the ILEA classification described below and in FIG. 1.

The International classification of seizure types proposed by the ILAE was adopted in 1981 and a revised proposal was published by the ILAE in 2010 and has not yet superseded the 1981 classification. FIG. 1 is adapted from the 2010 proposal for revised terminology and includes the proposed changes to replace the terminology of partial with focal. In addition the term "simple partial seizure" has been replaced by the term "focal seizure where awareness/responsiveness is not impaired" and the term "complex partial seizure" has been replaced by the term "focal seizure where awareness/consciousness is impaired".

From FIG. 1 it can be seen that Generalised seizures, where the seizure arises within and rapidly engages bilaterally distributed networks, can be split into six subtypes: Tonic-Clonic (grand mal) seizures; Absence (petit mal) Seizures; Clonic Seizures; Tonic Seizures; Atonic Seizures and Myoclonic Seizures.

Focal (partial) seizures where the seizure originates within networks limited to only one hemisphere, are also split into sub-categories. Here the seizure is characterized according to one or more features of the seizure, including aura, motor, autonomic and awareness/responsiveness. Where a seizure begins as a localized seizure and rapidly evolves to be distributed within bilateral networks this seizure is known as a bilateral convulsive seizure, which is the proposed terminology to replace Secondary Generalized Seizures (generalized seizures that have evolved from focal seizures and are no longer remain localized).

Focal seizures where the subject's awareness/responsiveness is altered are referred to as focal seizures with impairment and focal seizures where the awareness or responsiveness of the subject is not impaired are referred to as focal seizures without impairment.

Atonic seizures involve the loss of muscle tone, causing the person to fall to the ground. These are sometimes called 'drop attacks' and are usually brief (less than 15 seconds). Atonic seizures can occur without warning while standing, sitting and walking and the patient often suffers from trauma due to falling.

Atonic seizures are often associated with Lennox-Gastaut Syndrome but also occur, and may be symptomatic of other types of epileptic syndromes including: Tuberous Sclerosis Complex; Dravet Syndrome; Doose Syndrome; Aicardi syndrome; CDKL5 and Dup15q.

Epileptic syndromes often present with many different types of seizure and identifying the types of seizure that a patient is suffering from is important as many of the standard AED's are targeted to treat or are only effective against a given seizure type/sub-type.

One such childhood epilepsy syndrome is Lennox-Gastaut syndrome. Lennox-Gastaut syndrome is a severe form of epilepsy. Seizures usually begin before the age of 4. Seizure types, which vary among patients, include tonic (stiffening of the body, upward deviation of the eyes, dilation of the pupils, and altered respiratory patterns), atonic (brief loss of muscle tone and consciousness, causing abrupt falls), atypical absence (staring spells), and myoclonic (sudden muscle jerks). There may be periods of frequent seizures mixed with brief, relatively seizure-free periods.

Most children with Lennox-Gastaut syndrome experience some degree of impaired intellectual functioning or information processing, along with developmental delays, and behavioural disturbances.

Lennox-Gastaut syndrome can be caused by brain malformations, perinatal asphyxia, severe head injury, central nervous system infection and inherited degenerative or metabolic conditions. In 30-35 percent of cases, no cause can be found.

The first line treatment for atonic seizures, including the treatment of atonic seizures in patients with Lennox-Gastaut syndrome usually comprises a broad spectrum AED, such as sodium valproate often in combination with lamotrigine. Other AED that may be considered include rufinamide, felbamate, clobazam and topiramate.

AED such as carbamezapine, gabapentin, oxcarbazepine, pregabalin, tiagabine or and vigabatrin are contra-indicated in atonic seizures.

Common AED defined by their mechanisms of action are described in the following tables:

TABLE 1

Examples of narrow spectrum AED

| Narrow-spectrum AED | Mechanism | Indication |
| --- | --- | --- |
| Phenytoin | Sodium channel | Complex partial<br>Tonic-clonic |
| Phenobarbital | GABA/<br>Calcium channel | Partial seizures<br>Tonic-clonic |
| Carbamazepine | Sodium channel | Partial seizures<br>Tonic-clonic<br>Mixed seizures |

TABLE 1-continued

Examples of narrow spectrum AED

| Narrow-spectrum AED | Mechanism | Indication |
| --- | --- | --- |
| Oxcarbazepine | Sodium channel | Partial seizures<br>Tonic-clonic<br>Mixed seizures |
| Gabapentin | Calcium channel | Partial seizures<br>Mixed seizures |
| Pregabalin | Calcium channel | Adjunct therapy for partial seizures with or without secondary generalisation |
| Lacosamide | Sodium channel | Adjunct therapy for partial seizures |
| Vigabatrin | GABA | Secondarily generalized tonic-clonic seizures<br>Partial seizures<br>Infantile spasms due to West syndrome |

TABLE 2

Examples of broad spectrum AED

| Broad-spectrum AED | Mechanism | Indication |
| --- | --- | --- |
| Valproic acid | GABA/<br>Sodium channel | First-line treatment for tonic-clonic seizures, absence seizures and myoclonic seizures<br>Second-line treatment for partial seizures and infantile spasms.<br>Intravenous use in status epilepticus |
| Lamotrigine | Sodium channel | Partial seizures<br>Tonic-clonic<br>Seizures associated with Lennox-Gastaut syndrome |
| Topiramate | GABA/<br>Sodium channel | Seizures associated with Lennox-Gastaut syndrome |
| Zonisamide | GABA/<br>Calcium/<br>Sodium channel | Adjunctive therapy in adults with partial-onset seizures<br>Infantile spasm<br>Mixed seizure<br>Lennox-Gastaut syndrome<br>Myoclonic<br>Generalised tonic-clonic seizure |
| Levetiracetam | Calcium channel | Partial seizures<br>Adjunctive therapy for partial, myoclonic and tonic-clonic seizures |
| Clonazepam | GABA | Typical and atypical absences<br>Infantile myoclonic<br>Myoclonic seizures<br>Akinetic seizures<br>Atonic seizures |
| Rufinamide | Sodium channel | Adjunctive treatment of partial seizures associated with Lennox-Gastaut syndrome |

TABLE 3

Examples of AED used specifically in childhood epilepsy

| AED | Mechanism | Indication |
| --- | --- | --- |
| Clobazam | GABA | Adjunctive therapy in complex partial seizures |
| | | Status epilepticus |
| | | Myoclonic |
| | | Myoclonic-absent |
| | | Simple partial |
| | | Complex partial |
| | | Absence seizures |
| | | Lennox-Gastaut syndrome |
| Stiripentol | GABA | Severe myoclonic epilepsy in infancy (Dravet syndrome) |

From these tables it can be seen that there is only one drug currently approved for use in the treatment of atonic seizures, namely clonazepam. This medication works by the GABA mechanism.

Over the past forty years there have been a number of animal and human studies on the use of the non-psychoactive cannabinoid cannabidiol (CBD) to treat seizures.

A study in 1978 provided 200 mg/day of pure CBD to four adult patients, two of the four patients became seizure free, whereas in the remainder, seizure frequency was unchanged (Mechoulam and Carlini, 1978).

Cunha et al. reported that administration of CBD to eight adult patients with generalized epilepsy resulted in a marked reduction of seizures in 4 of the patients (Cunha et al., 1980) and Consroe et al., (1982) determined that CBD was able to prevent seizures in mice after administration of pro-convulsant drugs or an electric current.

In contrast to the studies described above, an open label study reported that 200 mg/day of pure CBD was ineffective in controlling seizures in twelve institutionalized adult patients (Ames and Cridland, 1986).

All of the studies described above focused on the treating subjects suffering from generalised epilepsy and did not look at the treatment of specific seizure sub-types.

More recently, WO 2011/001169 describes the use of CBD in the treatment of focal seizures, WO 2012/093255 describes the use of CBD in combination with standard anti-epileptic drugs in the treatment of epilepsy and WO 2013/045891 describes a composition comprising CBD and CBDV for use in the treatment of epilepsy.

In November 2013 the company GW Pharmaceuticals made a press release to state that they were intending to treat Dravet Syndrome with CBD as it had received orphan drug designation. The company made a further press release in February 2014 that that they were intending to treat Lennox-Gastaut Syndrome with CBD as it had also received orphan drug designation.

Again the rationale was to treat a disease as opposed to the type of seizure that the subject experienced.

It has additionally been suggested that *cannabis* which is enriched in CBD may be efficacious in the treatment of epilepsy. A case study of a child with Lennox-Gastaut syndrome showed improvement in seizure frequency after treatment with CBD in an oily solution was reported in 2005 (Pelliccia et al. 2005).

Porter and Jacobson (2013) report on a parent survey conducted via a Facebook group which explored the use of *cannabis* which was enriched with CBD in children with treatment-resistant epilepsy. It was found that sixteen of the 19 parents surveyed reported an improvement in their child's epilepsy. The children surveyed for this paper were all taking *cannabis* that was purported to contain CBD in a high concentration although the amount of CBD present and the other constituents including THC were not known for many of the cases. Indeed, whilst CBD levels ranged from 0.5 to 28.6 mg/kg/day (in those extracts tested), THC levels as high as 0.8 mg/kg/day were reported. Providing children with TRE with a *cannabis* extract that comprises THC, which has been described as a pro-convulsant (Consroe et al., 1977), at a potentially psychoactive dose of 0.8 mg/kg/day, is a concern.

In addition a paper published in June 2014 describes the use of a high-CBD strain to treat a patient with Dravet Syndrome; the patient's seizure frequency was stated to be reduced by the treatment (Maa et al. 2014).

A document published after the priority application was filed discloses the use of CBD in the treatment of refractory epilepsy in the treatment of Tuberous Sclerosis Complex in patients having focal onset seizures (Geffrey et al., 2014).

Whilst the potential of *cannabis* and the cannabinoids, including CBD, to treat epilepsy has been rekindled, to date there has been little in the way of real data to support its efficacy in patients.

The applicant has found that CBD shows significant efficacy in reducing atonic seizures, by greater than 50% in a large proportion, namely 63%, of patients. By way of comparison the proportion of patients benefitting from a greater than 50% reduction in total seizures was significantly less, (46%), in all subjects treated.

It is additionally worth noting that the patients being treated were treatment resistant to existing AED and so consequently these figures are even the more remarkable.

BRIEF SUMMARY OF THE DISCLOSURE

In accordance with a first aspect of the present invention there is provided cannabidiol (CBD) for use in the treatment of atonic seizures.

Preferably the atonic seizures are treatment-resistant.

Preferably the atonic seizures associated with Lennox-Gastaut Syndrome; Tuberous Sclerosis Complex; Dravet Syndrome; Doose Syndrome; Aicardi syndrome, CDKL5 or Dup15q.

In one embodiment the CBD is for use in combination with one or more concomitant anti-epileptic drugs (AED).

In a further embodiment the CBD is present as a highly purified extract of *cannabis* which comprises at least 95% (w/w) CBD, more preferably 98% (w/w) CBD. Preferably the extract comprises less than 0.15% THC. More preferably the extract further comprises up to 1% CBDV.

In an alternative embodiment the wherein the CBD is present as a synthetic compound.

In a further embodiment of the invention the one or more AED is selected from the group consisting of: clobazam; clonazepam, levetiracetam; topiramate; stiripentol; phenobarbital; lacsamide; valproic acid; zonisamide; perampanel; and fosphenytoin.

Preferably the number of different anti-epileptic drugs that are used in combination with the CBD is reduced. Alternatively the dose of the one or more anti-epileptic drugs that are used in combination with the CBD is reduced.

Preferably the dose of CBD is greater than 5 mg/kg/day.

In accordance with a second aspect of the present invention there is provided a method of treating atonic seizures comprising administering cannabidiol (CBD) to a subject.

In accordance with a third aspect of the present invention there is provided a composition for use in the treatment of atonic seizures characterised by atonic seizures comprising cannabidiol (CBD), a solvent, a co-solvent, a sweetener, and a flavouring.

Preferably the solvent is sesame oil, the co-solvent is ethanol, the sweetener is sucralose, the flavouring is strawberry flavour and the CBD is present at a concentration of between 25/mg/ml and 100 mg/ml.

More preferably the composition comprises cannabidiol (CBD) at a concentration of between 25 to 100 mg/ml, ethanol at a concentration of 79 mg/ml, sucralose at a concentration of 0.5 mg/ml, strawberry flavouring at a concentration of 0.2 mg/ml and sesame q.s. to 1.0 ml.

BRIEF DESCRIPTION OF THE DRAWINGS

FIG. 1 shows the ILEA 2010 proposal for revised terminology for organization of seizures and epilepsies.

DEFINITIONS

Definitions of some of the terms used to describe the invention are detailed below;

The cannabinoids described in the present application are listed below along with their standard abbreviations.

TABLE 4

Cannabinoids and their abbreviations

CBD  Cannabidiol
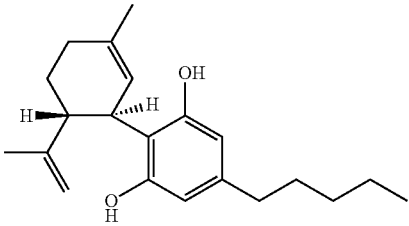 [SMILES: C=C(C)[C@@H]1CCC(C)=C[C@H]1c1c(O)cc(CCCCC)cc1O]

CBDA  Cannabidiolic acid
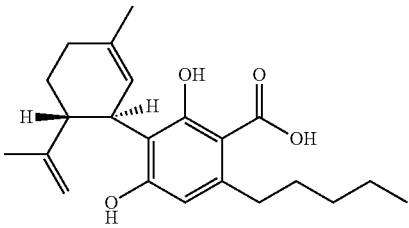 [SMILES: C=C(C)[C@@H]1CCC(C)=C[C@H]1c1c(O)cc(CCCCC)c(C(=O)O)c1O]

CBDV  Cannabidivarin
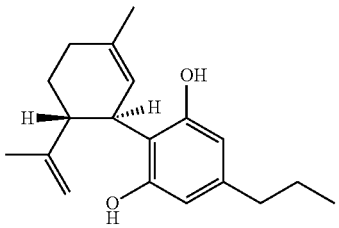 [SMILES: C=C(C)[C@@H]1CCC(C)=C[C@H]1c1c(O)cc(CCC)cc1O]

CBDVA  Cannabidivarinic acid
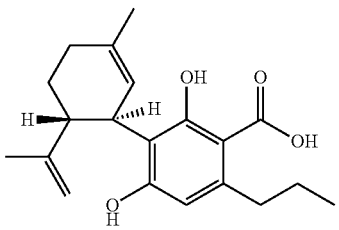 [SMILES: C=C(C)[C@@H]1CCC(C)=C[C@H]1c1c(O)cc(CCC)c(C(=O)O)c1O]

THC  Tetrahydrocannabinol
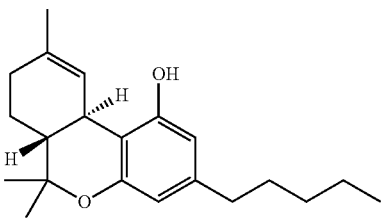 [SMILES: CCCCCc1cc(O)c2c(c1)OC(C)(C)[C@@H]1CCC(C)=C[C@@H]21]

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the *cannabis* plant. The phytocannabinoids can be isolated from plants to produce a highly purified extract or can be reproduced synthetically.

"Highly purified cannabinoids" are defined as cannabinoids that have been extracted from the *cannabis* plant and purified to the extent that other cannabinoids and non-cannabinoid components that are co-extracted with the cannabinoids have been removed, such that the highly purified cannabinoid is greater than or equal to 95% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example it is known that heating the carboxylic acid form will cause most of the carboxylic acid form to decarboxylate into the neutral form.

"Treatment-resistant epilepsy" (TRE) or "intractable epilepsy" is defined as per the ILAE guidance of 2009 as epilepsy that is not adequately controlled by trials of one or more AED.

"Childhood epilepsy" refers to the many different syndromes and genetic mutations that can occur to cause epilepsy in childhood. Examples of some of these are as follows: Dravet Syndrome: Myoclonic-Absence Epilepsy, Lennox-Gastaut syndrome; Generalized Epilepsy of unknown origin; CDKL5 mutation. Aicardi syndrome; bilateral polymicrogyria; Dup15q; SNAP25; and febrile infection related epilepsy syndrome (FIRES); benign rolandic epilepsy; juvenile myoclonic epilepsy: infantile spasm (west syndrome), and Landau-Kleffner syndrome. The list above is non-exhaustive as many different childhood epilepsies exist.

"Atonic Seizures" are defined as a convulsive type of epileptic seizure which causes the muscles to relax and the patient to flop or fall.

"Mixed seizures" are defined as the existence of both generalised and focal seizures in the same patient.

The terms "50% responder" and "50% reduction in seizure" are both terms used in clinical studies. In the present application the terms define the percentage of subjects that experienced a greater than or equal to 50% reduction in the number of seizures during treatment with CBD in comparison to the number experienced during the baseline period before the CBD was administered.

DETAILED DESCRIPTION

Preparation of Highly Purified CBD Extract

The following describes the production of the highly-purified (>98% w/w) cannabidiol extract which has a known and constant composition which was used for the expanded access trials described in Examples below.

In summary the drug substance used in the trials is a liquid carbon dioxide extract of high-CBD containing chemotypes of *Cannabis sativa* L. which had been further purified by a solvent crystallization method to yield CBD. The crystallisation process specifically removes other cannabinoids and plant components to yield greater than 95% CBD w/w, typically greater than 98% w/w.

The *Cannabis sativa* L. plants are grown, harvested, and processed to produce a botanical extract (intermediate) and then purified by crystallization to yield the CBD (drug substance).

The plant starting material is referred to as Botanical Raw Material (BRM); the botanical extract is the intermediate; and the active pharmaceutical ingredient (API) is CBD, the drug substance.

Both the botanical starting material and the botanical extract are controlled by specifications. The drug substance specification is described in Table 5 below.

TABLE 5

| CBD Specification | | |
|---|---|---|
| Test | Test Method | Limits |
| Appearance | Visual | Off-white/pale yellow crystals |
| Identification A | HPLC-UV | Retention time of major peak corresponds to certified CBD Reference Standard |
| Identification B | GC-FID/MS | Retention time and mass spectrum of major peak corresponds to certified CBD Reference Standard |
| Identification C | FT-IR | Conforms to reference spectrum for certified CBD Reference Standard |
| Identification D | Melting Point | 65-67° C. |
| Identification E | Specific Optical Rotation | Conforms with certified CBD Reference Standard; −110° to −140° (in 95% ethanol) |
| Total Purity | Calculation | ≥98.0% |
| Chromatographic Purity 1 | HPLC-UV | ≥98.0% |
| Chromatographic Purity 2 | GC-FID/MS | ≥98.0 % |
| Other Cannabinoids: | HPLC-UV | |
| CBDA | | NMT 0.15% w/w |
| CBDV | | NMT 1.0% w/w |
| $\Delta^9$ THC | | NMT 0.15% w/w |
| CBD-C4 | | NMT 0.5% w/w |
| Residual Solvents: | GC | |
| Alkane | | NMT 0.5% w/w |
| Ethanol | | NMT 0.5% w/w |
| Residual Water | Karl Fischer | NMT 1.0% w/w |

NMT-Not more than

The purity of the CBD drug substance achieved is greater than 98%. The other cannabinoids which may occur in the extract are: CBDA, CBDV, CBD-C4 and THC.

Distinct chemotypes of *Cannabis sativa* L. plant have been produced to maximize the output of the specific chemical constituents, the cannabinoids. One type of plant produces predominantly CBD. Only the (−)-trans isomer occurs naturally, furthermore during purification the stereochemistry of CBD is not affected.

Production of the Intermediate

An overview of the steps to produce a botanical extract, the intermediate, are as follows:
1. Growing
2. Decarboxylation
3. Extraction No. 1—using liquid $CO_2$
4. Extraction No. 2—'winterization' using ethanol
5. Filtration
6. Evaporation High CBD chemovars were grown, harvested and dried and stored in a dry room until required. The botanical raw material (BRM) was finely chopped using an Apex mill fitted with a 1 mm screen. The milled BRM was stored in a freezer for up to 3 months prior to extraction.

Decarboxylation of CBDA to CBD was carried out using a large Heraeus tray oven. The decarboxylation batch size in the Heraeus is approximately 15 Kg. Trays were placed in the oven and heated to 105° C.; the BRM took 96.25 minutes to reach 105° C. Held at 105° C. for 15 Minutes. Oven then set to 150° C.; the BRM took 75.7 minutes to reach 150° C.; BRM held at 150° C. for 130 Minutes. Total time in the oven was 380 Minutes, including 45 minutes cooling and 15 Minutes venting.

Extraction No 1 was performed using liquid $CO_2$ at 60 bar/10° C. to produce botanical drug substance (BDS) which was used for crystallisation to produce the test material.

The crude CBD BDS was winterised in Extraction No 2 under standard conditions (2 volumes of ethanol at minus 20° C. for around 50 hours). The precipitated waxes were removed by filtration and the solvent evaporated using the rotary evaporator (water bath up to 60° C.) to yield the BDS.

Production of the Drug Substance

The manufacturing steps to produce the drug substance from the intermediate botanical extract are as follows:
1. Crystallization using C5-C12 straight chain or branched alkane
2. Filtration
3. Optional recrystallization from C5-C12 straight chain or branched alkane
4. Vacuum drying Intermediate botanical extract (12 kg) produced using the methodology above was dispersed in C5-C12 straight chain or branched alkane (9000 ml, 0.75 vols) in a 30 litre stainless steel vessel.

The mixture was manually agitated to break up any lumps and the sealed container then placed in a freezer for approximately 48 hours.

The crystals were isolated by vacuum filtration, washed with aliquots of cold C5-C12 straight chain or branched alkane (total 12000 ml), and dried under a vacuum of <10 mb at a temperature of 60° C. until dry before submitting the drug substance for analysis. The dried product was stored in a freezer at minus 20° C. in a pharmaceutical grade stainless steel container, with FDA food grade approved silicone seal and clamps.

Production of the Drug Product

The drug product is presented as an oral solution. The oral solution presentation contains 25 mg/ml or 100 mg/ml CBD, with the excipients sesame oil, ethanol, sucralose and flavouring. Two product strengths are available to allow dose titration across a wide dose range.

The 25 mg/ml solution is appropriate at lower doses and the 100 mg/ml solution at higher doses.

The drug product formulation is as described in Table 6 below:

TABLE 6

Drug Product specification

| Component | Qualitative Composition | Function | Reference to Quality Standard |
|---|---|---|---|
| Cannabidiol (CBD) | 25 mg/ml or 100 mg/ml | Active | In-house |
| Anhydrous ethanol | 79.0 mg/ml* | Excipient | Ph.Eur. |
| Sucralose | 0.5 mg/ml | Sweetener | In-house |

TABLE 6-continued

Drug Product specification

| Component | Qualitative Composition | Function | Reference to Quality Standard |
|---|---|---|---|
| Strawberry flavouring | 0.2 mg/ml | Flavouring | In-house |
| Sesame oil | q.s to 1.0 ml | Excipient | Ph.Eur. |

The drug substance, CBD is insoluble in water. Sesame oil was selected as an excipient to solubilize the drug substance.

A sweetener and fruit flavouring are required to improve palatability of the sesame oil solution.

Ethanol was required to solubilize the sweetener and the flavouring.

The composition can be substantially equivalent, by which is meant the functional ingredients can vary from the qualitative composition specified in Table 6 by an amount of up to 10%.

Example 1 below describes the use of a highly purified *cannabis* extract comprising cannabidiol (CBD) in an expanded access treatment program in children with TRE.

Example 1: Efficacy of Cannabidiol Reducing Atonic Seizures in Children and Young Adults with Intractable Epilepsy Materials and Methods Of 137 children and young adults with severe, childhood onset treatment-resistant epilepsy (TRE), twenty-seven suffered from epilepsy that was characterised by atonic seizures. These subjects were tested with a highly purified extract of cannabidiol (CBD) obtained from a *cannabis* plant. All subjects presented with atonic type seizures, often in addition to other seizures. The participants in the study were part of an expanded access compassionate use program for CBD.

The epileptic syndromes that these patients suffered from were as follows: Lennox-Gastaut Syndrome; Tuberous Sclerosis Complex; Dravet Syndrome: Doose Syndrome; Aicardi syndrome, CDKL5 and Dup15q.

All patients entered a baseline period of 4 weeks when parents/caregivers kept prospective seizure diaries, noting all countable seizure types.

The patients then received a highly purified CBD extract (greater than 98% CBD w/w) in sesame oil, of known and constant composition, at a dose of 5 mg/kg/day in addition to their baseline anti-epileptic drug (AED) regimen.

The daily dose was gradually increased by 2 to 5 mg/kg increments until intolerance occurred or a maximum dose of 25 mg/kg/day was achieved.

Patients were seen at regular intervals of 2-4 weeks. Laboratory testing for hematologic, liver, kidney function, and concomitant AED levels was performed at baseline, and after 4 weeks of CBD therapy.

All patients were taking at least two concomitant anti-epileptic drugs. These included clobazam; levetiracetam; topiramate; stiripentol; phenobarbital; lacsamide; valproic acid; zonisamide. The average number of concomitant anti-epileptic drugs being taken was 2.7. The majority took either clobazam and/or valproic acid.

Results

There were 27 children and young adult patients all of whom suffered from atonic seizures received treatment with CBD for at least 12 weeks.

A summary of the 50% responders, based on 12 weeks of treatment are summarized in Table 7 below.

TABLE 7

Summary of 50% responders after 12 weeks of treatment for atonic seizures

|  | Atonic seizures (n = 27) | Total seizures (n = 137) |
|---|---|---|
| >50% reduction in seizures | 63% (n = 17) | 46% (n = 63) |
| <50% reduction in seizures | 37% (n = 10) | 54% (n = 74) |

Table 7 shows that after 3 months of therapy, a remarkable 63% of patients had an equal to or greater than >50% reduction in atonic seizures, these data infer that the CBD is very effective at reducing this type of seizure.

CONCLUSIONS

These data indicate that CBD significantly reduces the number of atonic seizures in a high proportion of patients that do not respond well to existing AED.

It was surprising that in this group of patients which are treatment-resistant such a high number were able to gain an effect. The fact that nearly two thirds of the patients (63%) benefitted from at least a fifty percent reduction in the number of atonic seizures that they suffered from was remarkable.

Furthermore when these data are compared to the other sub-types of generalised seizure, it can clearly be seen that CBD was able to selectively reduce the occurrence of atonic seizures. Table 8 below details these findings.

TABLE 8

Summary of 50% responders after 12 weeks of treatment for all seizure sub-types

|  | Atonic seizures (n = 27) | Tonic seizures (n = 45) | Tonic-clonic seizures (n = 65) | Clonic seizures (n = 8) | Myoclonic seizures (n = 30) | Absence seizures (n = 28) |
|---|---|---|---|---|---|---|
| >50% reduction in seizures | 63% (n = 17) | 49% (n = 22) | 43% (n = 28) | 50% (n = 4) | 43% (n = 13) | 64% (n = 18) |
| <50% reduction in seizures | 37% (n = 10) | 51% (n = 23) | 37% (n = 37) | 50% (n = 4) | 57% (n = 17) | 36% (n = 10) |

From Table 8 it can be seen that when the number of atonic seizures recorded is compared with other generalised seizure types such as tonic seizures (49% of patients experienced a greater than 50% reduction in seizure), tonic-clonic seizures (43% of patients experienced a greater than 50% reduction in seizure), and myoclonic seizures (43% of patients experienced a greater than 50% reduction in seizure) the fact that nearly two thirds (63%) of patients experiencing atonic seizures had a greater than 50% reduction in the number of seizures that occurred is very surprising.

REFERENCES

Ames F R and Cridland S (1986). "Anticonvulsant effects of cannabidiol." S Aft Med J 69:14.
Consroe P, Martin P, Eisenstein D. (1977). "Anticonvulsant drug antagonism of delta-9-tetrahydrocannabinol induced seizures in rabbits." Res Commun Chem Pathol Pharmacol. 16:1-13
Consroe P, Benedicto M A, Leite J R. Carlini E A, Mechoulam R. (1982). "Effects of cannabidiol on behavioural seizures caused by convulsant drugs or current in mice." Eur J Pharmaco. 83: 293-8
Cunha J M, Carlini E A, Pereira A E, Ramos O L, Pimental C, Gagliardi R et al. (1980). "Chronic administration of cannabidiol to healthy volunteers and epileptic patient." Pharmacology. 21:175-85
Dravet C. The core Dravet syndrome phenotype. Epilepsia. 2011 April; 52 Suppl 2:3-9.
Eadie, MJ (December 2012). "Shortcomings in the current treatment of epilepsy." Expert Review of Neurotherapeutics 12 (12): 1419-27.
Geffrey A, Pollack S, Paolini J, Bruno P, Thiele E (2014) "Cannabidiol (CBD) treatment for refractory epilepsy in Tuberous Sclerosis Complex (TSC)." American Epilepsy Society Annual Meeting. 5-9 Dec. 2014.
Kwan P, Arzimanoglou A, Berg A T, Brodie M J, Hauser W A, Mathem G, Moshé SL, Perucca E, Wiebe S, French J. (2009) "Definition of drug resistant epilepsy: Consensus proposal by the ad hoc Task Force of the ILAE Commission on Therapeutic Strategies." Epilepsia.
Maa E and Figi P (2014). "The case for medical marijuana in epilepsy", Epilepsia 55(6):783-786
Mechoulam R and Carlini E A (1978). "Toward drugs derived from cannabis." Die naturwissenschaften 65:174-9.
Pelliccia A, Grassi G, Romano A, Crocchialo P (2005). "Treatment with CBD in oily solution of drug resistant paediatric epilepsies". Congress of Cannabis and the Cannabinoids, Leiden, The Netherlands. International Association for Cannabis as a Medicine. p14.
Porter B E, Jacobson C (December 2013). "Report of a parent survey of cannabidiol-enriched cannabis use in paediatric treatment resistant epilepsy" Epilepsy Behaviour. 29(3) 574-7
Thurman, DJ; Beghi, E; Begley, CE; Berg, AT; Buchhalter, JR; Ding, D; Hesdorffer, DC; Hauser, WA; Kazis, L; Kobau, R; Kroner, B; Labiner, D; Liow, K; Logroscino, G; Medina, MT; Newton, CR; Parko, K; Paschal, A; Preux, P M; Sander, J W; Selassie, A; Theodore, W; Tomson, T; Wiebe, S; ILAE Commission on, Epidemiology (September 2011). "Standards for epidemiologic studies and surveillance of epilepsy." Epilepsia. 52 Suppl 7: 2-26

What is claimed:
1. A method of treating seizures associated with juvenile myoclonic epilepsy in a patient in need thereof, comprising administering to the patient a pharmaceutical composition comprising a cannabidiol (CBD) drug substance, wherein the CBD drug substance comprises at least 98% w/w CBD; and
    wherein the dose of CBD administered to the patient ranges from about 5 mg/kg/day to about 25 mg/kg/day.
2. The method of claim 1, wherein the CBD drug substance comprises not more than 0.15% w/w CBDA.
3. The method of claim 1, wherein the CBD drug substance comprises not more than 1.0% w/w CBDV.

4. The method of claim 1, wherein the CBD drug substance comprises not more than 0.15% w/w Δ9THC.

5. The method of claim 1, wherein the CBD drug substance comprises not more than 0.5% w/w CBD-C4.

6. The method of claim 1, wherein the CBD drug substance comprises not more than 1.0% w/w CBDV and not more than 0.15% w/w Δ9THC.

7. The method of claim 1, wherein the CBD drug substance comprises not more than 1.0% w/w CBDV, not more than 0.15% w/w Δ9THC, and not more than 0.5% w/w CBD-C4.

8. The method of claim 1, wherein the CBD drug substance comprises not more than 0.15% w/w CBDA, not more than 1.0% w/w CBDV, not more than 0.15% w/w Δ9THC, and not more than 0.5% w/w CBD-C4.

9. The method of claim 1, wherein the administering reduces the number of seizures compared to baseline.

10. The method of claim 1, wherein the administering reduces total seizure frequency compared to baseline.

11. The method of claim 1, wherein the administering reduces total seizure frequency by at least 50% compared to baseline.

12. The method of claim 8, wherein the administering reduces the number of seizures compared to baseline.

13. The method of claim 8, wherein the administering reduces total seizure frequency compared to baseline.

14. The method of claim 8, wherein the administering reduces total seizure frequency by at least 50% compared to baseline.

15. The method of claim 1, wherein the dose of CBD is about 10 mg/kg/day.

16. The method of claim 15, wherein the administering reduces the number of seizures compared to baseline.

17. The method of claim 15, wherein the administering reduces total seizure frequency compared to baseline.

18. The method of claim 15, wherein the administering reduces total seizure frequency by at least 50% compared to baseline.

19. The method of claim 1, wherein the dose of CBD is about 20 mg/kg/day.

20. The method of claim 19, wherein the administering reduces the number of seizures compared to baseline.

21. The method of claim 19, wherein the administering reduces total seizure frequency compared to baseline.

22. The method of claim 19, wherein the administering reduces total seizure frequency by at least 50% compared to baseline.

23. The method of claim 1, wherein the dose of CBD administered to the patient is about 25 mg/kg/day.

24. The method of claim 23, wherein the administering reduces the number of seizures compared to baseline.

25. The method of claim 23, wherein the administering reduces total seizure frequency compared to baseline.

26. The method of claim 23, wherein the administering reduces total seizure frequency by at least 50% compared to baseline.

27. The method of claim 1, wherein the pharmaceutical composition is an oral solution comprising the cannabidiol (CBD) drug substance.

28. The method of claim 1, wherein the seizures comprise tonic-clonic seizures, myoclonic seizures, absence seizures, or a combination thereof.

29. The method of claim 1, wherein the CBD drug substance comprises synthetic CBD.

* * * * *